| United States Patent [19] | [11] Patent Number: 4,739,050 |
|---|---|
| Jun-ichi et al. | [45] Date of Patent: Apr. 19, 1988 |

[54] 2-PHENYL-1,4-BENZOTHIAZIN-3-ONE DERIVATIVES

[75] Inventors: Iwao Jun-ichi, Takarazuka; Iso Tadashi, Sakai; Oya Masayuki, Ibaraki, all of Japan

[73] Assignee: Santen Pharmaceutical Co., Ltd., Osaka, Japan

[21] Appl. No.: 928,277

[22] PCT Filed: Feb. 24, 1986

[86] PCT No.: PCT/JP86/00088

§ 371 Date: Nov. 4, 1986

§ 102(e) Date: Nov. 4, 1986

[87] PCT Pub. No.: WO86/05490

PCT Pub. Date: Sep. 25, 1986

[30] Foreign Application Priority Data

Mar. 19, 1985 [JP] Japan .................................. 60-55005

[51] Int. Cl.⁴ .................... C07D 279/10; A61K 31/38
[52] U.S. Cl. ...................................................... 544/52
[58] Field of Search .......................... 544/52; 514/225

[56] References Cited

U.S. PATENT DOCUMENTS

| 3,089,872 | 5/1963 | Krapcho | 544/52 |
| 3,401,166 | 9/1968 | Krapcho | 544/52 |
| 3,622,572 | 11/1971 | Krapcho | 544/52 |
| 4,595,685 | 6/1986 | Henning et al. | 544/52 |

FOREIGN PATENT DOCUMENTS

| 56-51465 | 5/1981 | Japan | 544/52 |
| 60-156679 | 8/1985 | Japan | 544/52 |

OTHER PUBLICATIONS

*Chemical Abstracts*, vol. 95, No. 115577x.
"Non-stereospecific Ring Expansion Reactions of Benzothiazoline Sulfoxides", *Chemical Pharmaceutical Bulletin*, vol. 32, No. 7, 1984, by Hiroshi Shimizu et al., pp. 2571–2590.

*Primary Examiner*—Henry R. Jiles
*Assistant Examiner*—J. G. Mullins
*Attorney, Agent, or Firm*—Young & Thompson

[57] ABSTRACT

This invention relates to 2-arylbenzothiazine derivatives of the formula[I] and salts thereof, process of preparation and therapeutic drug comprising them for circulatory diseases,

[I]

wherein $R^1$ and $R^2$ are the same or different and are hydrogen, lower alkyl, hydroxy, lower alkoxy, acyloxy, tetrahydropyranyloxy, halogen, nitro, amino, lower alkylamino or $$-O-B-N\begin{matrix}R^5\\R^6\end{matrix},$$

and the lower alkoxy group may be substituted by halogen, formyl, lower alkoxy or epoxy;

$R^3$ is hydrogen or lower alkyl;

$R^4$ is hydrogen, lower alkyl, cycloalkyl, hydroxy, lower alkoxy, mercapto, lower alkylthio, arylthio, halogen, cyano, formyl-lower alkyl, lower alkoxy-lower alkyl or $$-N\begin{matrix}R^7\\R^8\end{matrix};$$

$R^5, R^6, R^7$ and $R^8$ are the same or different and are hydrogen, lower alkyl, cycloalkyl, acyl, phenyl, pyridyl or substituted lower alkyl, and the phenyl or pyridyl group may be substituted by lower alkyl, hydroxy, lower alkoxy, lower alkylenedioxy, halogen, nitro, cyano, lower alkanoyloxy or halogeno-lower alkyl, and the substituent(s) of the substituted lower alkyl is(are) hydroxy, phenyl, phenyloxy, phenylcarbonyl or pyridyl, and such phenyl ring of the phenyl, phenyloxy or phenylcarbonyl group and the pyridyl group may further be resubstituted by lower alkyl, hydroxy, lower alkoxy, lower alkylenedioxy, halogen, nitro, cyano, lower alkanoyloxy or halogeno lower alkyl;

$R^5$ and $R^6$, and $R^7$ and $R^8$ may join to form piperidine, piperazine or morpholine ring, and the piperidine or piperazine ring may be substituted by lower alkyl, phenyl, hydroxy-lower alkyl, phenyl-lower alkyl, phenylcarbonyl, phenylcarbonyl-lower alkyl, spheny-(hydroxy) lower alkyl, phenyl-lower alkenylcarbonyl or naphthoxy-(hydroxy)lower alkyl, and such phenyl ring of the phenyl, phenyl-lower alkyl, phenylcarbonyl, phenylcarbonyl-lower alkyl, phenyl-(hydroxy)lower alkyl or phenyl-lower alkenylcarbonyl group may further be resubstituted by lower alkyl, lower alkoxy, alkylenedioxy or halogen;

Z is hydrogen, lower alkyl, lower alkoxy, hydroxy, halogen, cyano, nitro, halogeno-lower alkyl or lower alkanoyloxy;

A is straight or branched lower alkylene;

B is straight or branched lower alkylene which may be substituted by hydroxy; and n is 0 or 1, and when n is 0, both $R^4$ and Z are not represent hydrogen atom at the same time.

28 Claims, No Drawings

2-PHENYL-1,4-BENZOTHIAZIN-3-ONE DERIVATIVES

FIELD OF THE ART

This invention relates to 2-arylbenzothiazine derivatives which possess calcium antagonisum and anti-platelet aggregation effects and are useful for treating circulatory diseases.

BACKGROUND OF THE INVENTION

As the prior art concerning benzothiazone compounds which are useful for treating circulatory diseases, there exists the publication of European Patent Application (publication No. 116368) disclosing the compounds having 3-oxo-2H-1,4-benzothiazine as the main structure, which appears in the compounds of the present application.

However, such publication discloses only 2-mono substitutes and does not represent 2,2-disubstituted benzothiazine or benzothiazine derivatives having the substituent(s) at 5 to 8 position(s) as in the present application.

There was few studies on 2,2-disubstituted benzothiazine or benzothiazine derivatives having the substituent(s) at 5 to 8 position(s), so the necessity arose studing methods of synthesis and efficacy of such derivatives.

We synthesized a series of 2,2-disubstituted benzothiazine and benzothiazine derivatives having the substituent(s) at 5 to 8 position(s), and examined the efficacy thereof.

DISCLOSURE OF THE INVENTION

This invention relates to 2-arylbenzothiazine derivatives and salts thereof represented by the formula[I], processes of preparation and therapeutic drugs comprising them for treating circulatory diseases,

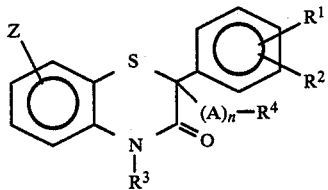

wherein
$R^1$ and $R^2$ are the same or different and are hydrogen, lower alkyl, hydroxy, lower alkoxy, acyloxy, tetrahydropyranyloxy, halogen, nitro, amino, lower alkylamino or

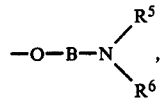

and the lower alkoxy group may be substituted by halogen, formyl, lower alkoxy or epoxy;
$R^3$ is hydrogen or lower alkyl;
$R^4$ is hydrogen, lower alkyl, cycloalkyl, hydroxy, lower alkoxy, mercapto, lower alkylthio, arylthio, halogen, cyano, formyl-lower alkyl, lower alkoxy-lower alkyl or

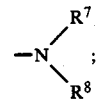

$R^5$, $R^6$, $R^7$ and $R^8$ are the same or different and are hydrogen, lower alkyl, cycloalkyl, acyl, phenyl, pyridyl or substituted lower alkyl, and the phenyl or pyridyl group may be substituted by lower alkyl, hydroxy, lower alkoxy, lower alkylenedioxy, halogen, nitro, cyano, lower alkanoyloxy or halogeno-lower alkyl, and the substituent(s) of the substituted lower alkyl is(are) hydroxy, phenyl, phenyloxy, phenylcarbonyl or pyridyl, and such phenyl ring of the phenyl, phenyloxy or phenylcarbonyl group and the pyridyl group may further be resubstituted by lower alkyl, hydroxy, lower alkoxy, lower alkylenedioxy, halogen, nitro, cyano, lower alkanoyloxy or halogeno-lower alkyl;
$R^5$ and $R^6$, and $R^7$ and $R^8$ may join to form piperidine, piperazine or morpholine ring, and the piperidine or piperazine ring may be substituted by lower alkly, phenyl, hydroxy-lower alkyl, phenyl-lower alkyl, phenylcarbonyl, phenylcarbonyl-lower alkyl, phenyl-(hydroxy)lower alkyl, phenyl-lower alkenylcarbonyl or naphthoxy-(hydroxy)lower alkyl, and such phenyl ring of the phenyl, phenyl-lower alkyl, phenylcarbonyl, phenylcarbonyl-lower alkyl, phenyl-(hydroxy)lower alkyl or phenyl-lower alkenylcarbonyl group may further be resubstituted by lower alkyl, lower alkoxy, alkylenedioxy or halogen;
Z is hydrogen, lower alkyl, lower alkoxy, hydroxy, halogen, cyano, nitro, halogeno-lower alkyl or lower alkanoyloxy;
A is straight or branched lower alkylene;
B is straight or branched lower alkylene which may be substituted by hydroxy; and
n is 0 to 1, and when n is 0, both $R^4$ and Z are not represent hydrogen atom at the same time.

The above mentioned groups are described more in detail as follows.

Lower alkyl means alkyl group having 1 to 6 carbon atoms such as methyl, ethyl, propyl, isopropyl, butyl, isobutyl and hexyl; lower alkoxy means alkoxy group having 1 to 6 carbon atoms such as methoxy, ethoxy, propoxy, butoxy and hexyloxy; acyloxy means alkanoyloxy group having 1 to 6 carbon atoms such as acetoxy, propionyloxy, butanoyloxy and pentanoyloxy, and aromatic carbonyloxy such as benzoyloxy; halogen means fluorine, chlorine, bromine and iodine; cycloalkyl means cycloalkyl group having 3 to 6 carbon atoms such as cyclopropane and cyclohexane; aryl means aromatic group such as phenyl and toryl; acyl means alkanoyl group having 1 to 6 carbon atoms such as acetyl, propionyl, butanoyl and pentanoyl, or aromatic carbonyl such as benzoyl; lower alkylenedioxy means alkylenedioxy group having 1 to 3 carbon atoms such as methylenedioxy, ethylenedioxy and propylenedioxy; lower alkanoyloxy means alkanoyloxy group having 1 to 6 carbon atoms such as acetoxy, propionyloxy, butanoyloxy and pentanoyloxy; lower alkenyl means alkenyl group having 2 to 6 carbon atoms such as ethylenyl and propenyl; lower alkylene means alkylene group having 1 to 6 carbon atoms such as methylene, ethylene, propylene, isopropylene, butylene and hexylene; and the meaning of lower alkyl described as a part of substituent is the same as the above mentioned lower alkyl. The same shall be applied hereinafter.

The compounds of this invention are novel benzothiazine derivatives which have not been disclosed in any literature, and are characterized in that the benzothiazine ring has two kinds of substituents at the 2-position or has substituent(s) at 5 to 8 position.

The compounds of this invention are useful for treating circulatory diseases such as hypertension, angina pectoris, arrhythmia and thrombosis. Calcium antagonist, inhibitor of platelet aggregation, β-blocker, etc. are used as therapeutic agents for circulatory diseases.

By the pharmacological tests described later, it is proved that the compounds of this invention possess superior calcium antagonism and anti-platelet aggregation efffects, so they are useful as therapeutic agents for treating circulatory diseases.

The compounds of this invention can be prepared by a combination of the known methods.

Examples of preparation are shown below.

The compounds of the formula[I] are prepared by a reaction of halide of the formula[II] with the compound of the formula[III],

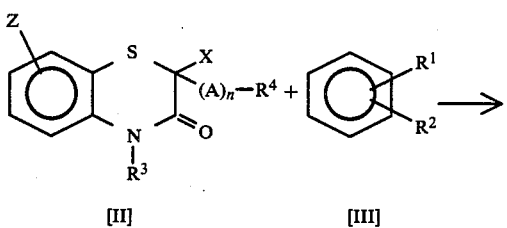

[II]   [III]

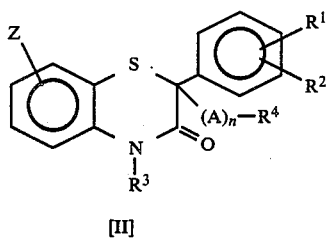

[I]

wherein X is halogen. The same shall be applied hereinafter.

The reaction is Friedel-Crafts like reaction, which is completed without specific catalyst, but if necessary, Lewis acid such as AlCl₃ can be used as a catalyst.

The starting compound represented by the formula[II] can be prepared by a reaction of halogenide such as sulfuryl chloride to introduce halogen atom at the 2-position of the benzothiazine ring.

Depending on the substituents, if necessary, the following (A) to (F) reaction is incorporated.

(A) The compound of the formula[I] wherein R⁴ is halogen and n is 0, that is represented by the formula[V], can be prepared by a reaction of the compound of the formula[V] with halogenide such as sulfuryl chloride in an organic solvent exemplified by methylene chloride.

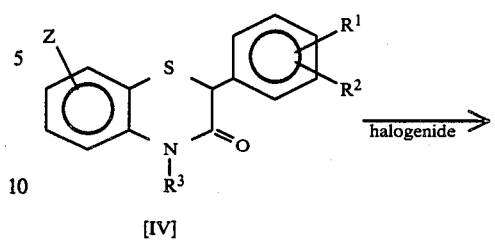

[IV]

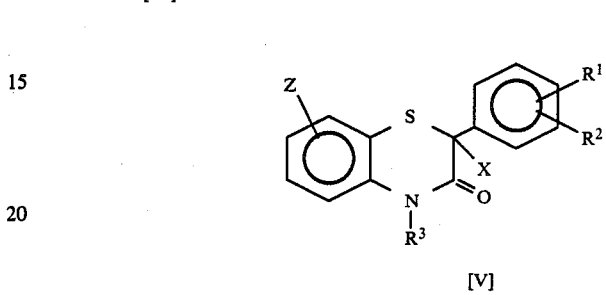

[V]

The compound of the formula[V], if necessary, can be used for the following reaction.

Nucleophilic reagent is reacted with the compound of the formula[V] to produce the compound of the formula[VI].

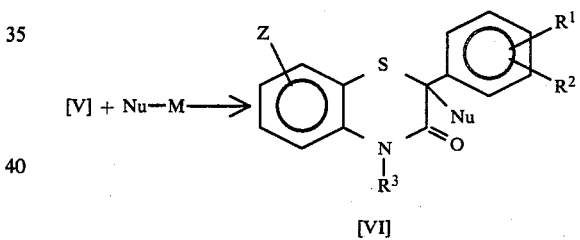

[VI]

wherein Nu is nucleophile and M is hydrogen or alkali metal (the same shall be applied hereinafter). Nucleophile is hydroxy, lower alkyl, cycloalkyl, lower alkoxy, mercapto, lower alkylthio, arylthio, cyano, formyl-lower alkyl, lower alkoxy-lower alkyl or

The reaction can be performed in water, an organic solvent or the mixture thereof, or without a solvent.

(B) The compound of the formula[IV] is reacted in an organic solvent with halogeno derivative of the formula[VII] in the presence of a base such as sodium hydride to produce the compound of the formula[VIII].

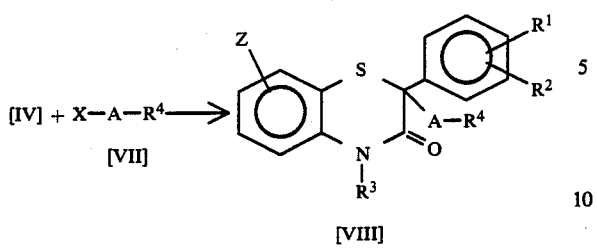

[IV] + X—A—R⁴ → [VII]

[VIII]

When R⁴ in the formula[VIII] represents halogen (formula[IX]), if necessary, the compound is reacted with nucleophilic reagent to produce the compound of the formula[X],

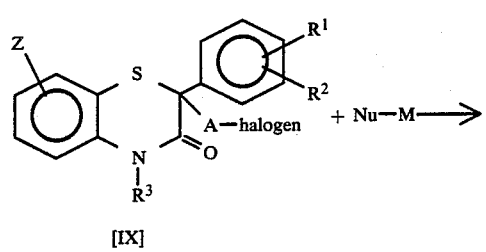

[IX] + Nu—M →

[X]

wherein the definition of Nu is the same in the method(A).

The reaction can be performed in water, an organic solvent or the mixture thereof, if necessary, in the presence of a base such as sodium carbonate, and if further necessary, the reaction is completed with the use of a catalyst such as sodium iodide.

(C) When R¹ or R² in the formula[I] represents hydroxy (to make an explanation simple, the compound is represented by the formula [XI], defining R¹ as hydroxy), if necessary, the following (a) to (d) reactions may follow, (a)

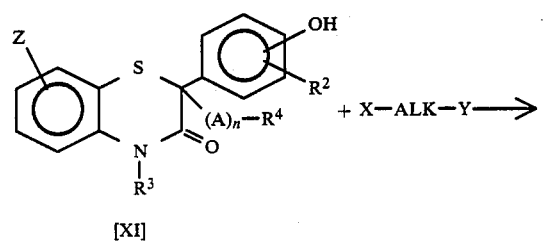

[XI] + X—ALK—Y →

-continued

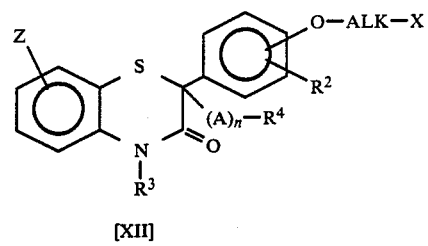

[XII]

wherein Y is halogen or methanesulfonyloxy and ALK is lower alkylene which may be substituted by hydroxy (the same shall be applied hereinafter). The reaction can be performed in the presence of a base such as sodium hydride and in an organic solvent.

The compound of the formula[XII], if necessary, is reacted with amine derivative in an organic solvent and in the presence of a base such as sodium carbonate, and if necessary, the reaction is completed with the use of a catalyst such as sodium iodide to produce the compound of the formula[XIII].

[XII] + HN(R⁵)(R⁶) →

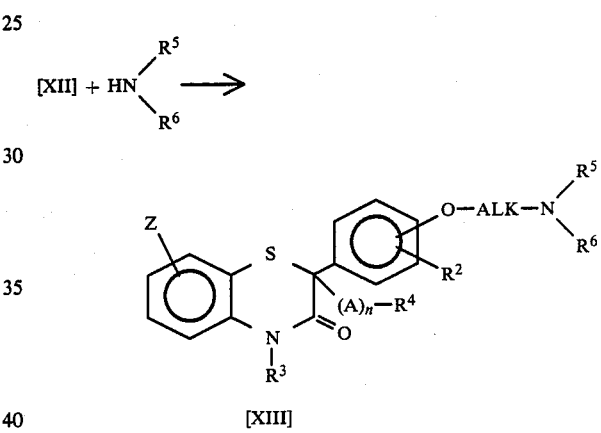

[XIII]

(b) The compound of the formula[XI] is reacted with the compound of the formula[XIV] in an organic solvent in the presence of a base such as sodium hydride to produce the compound of the formula[XV].

[XI] + Y—B—N(R⁵)(R⁶) →

[XIV]

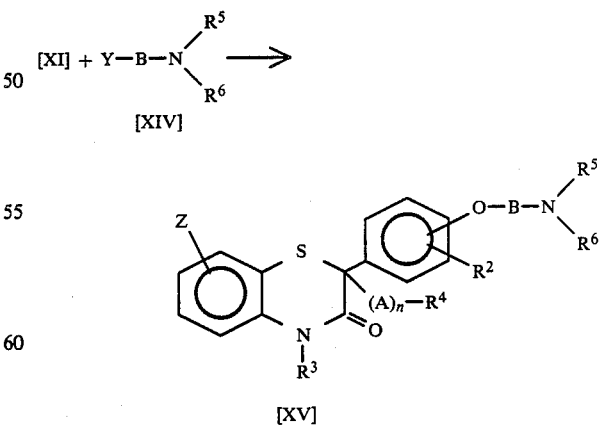

[XV]

(c) The compound of the formula[XI] is reacted with the epoxy derivative of the formula[XVI] in an organic solvent in the presence of a base such as sodium hydride to produce the compound of the formula[XVII].

The compound of the formula[XVII], if necessary, can be reacted with the amine derivative to produce the compound of the formula[XVIII].

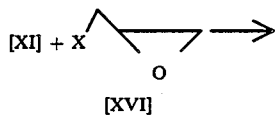

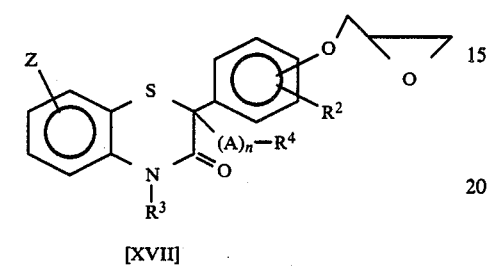

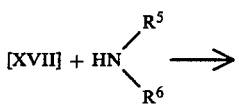

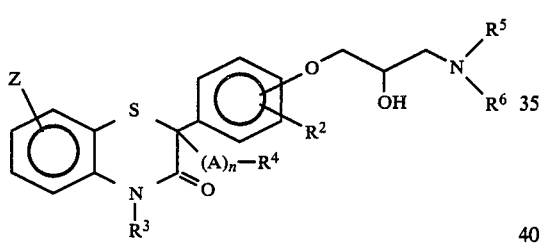

(d) The compound of the formula[XI] is reacted with the compound of the formula[XIX] in an organic solvent in the presence of a base such as sodium hydride to produce the compound of the formula[XX].

The compound of the formula[XX], if necessary, can be hydrolyzed by using the ion-exchange resin to produce the compound of the formula[XXI].

The compound of the formula[XXI], if further necessary, can be reacted with the amine derivative in the presence of a reducing agent such as sodium cyanoborohydride to produce the compound of the formula[XXII],

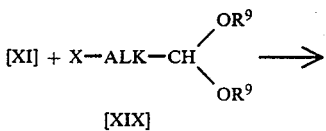

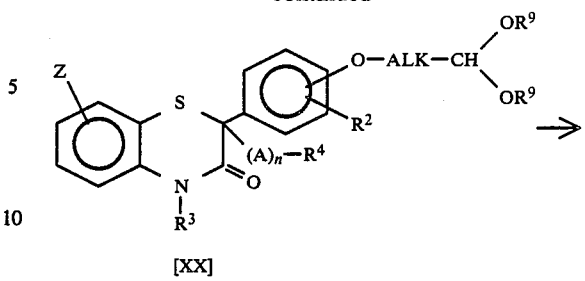

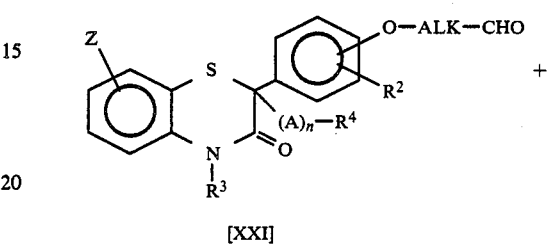

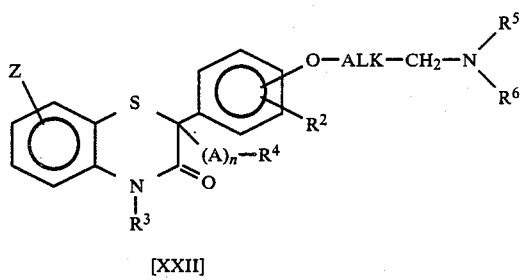

wherein $R^9$ is lower alkyl (the same shall be applied hereinafter).

(D) The compound of the formula[IV] is treated by the similar procedure of the method of (C)-(d) to produce the compounds of the formulas[XXIII], [XXIV] and [XXV].

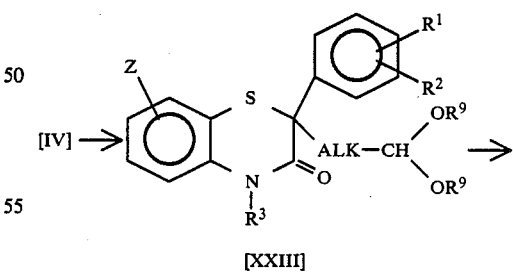

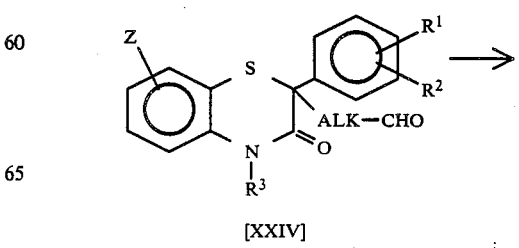

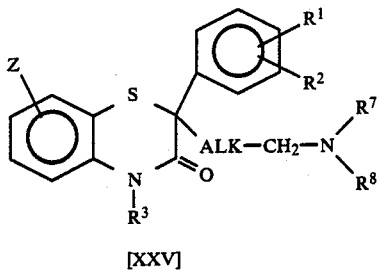

[XXV]

(E) The compound of the formula[I] wherein $R^1$ is

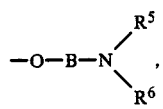

—(A)—$R^4$ is

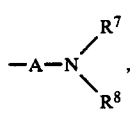

A and B are the same (represented by ALK) and

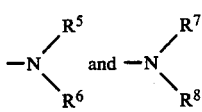

are the same (represented by Am), which is represented by the formula[XXVIII], can be prepared by the reaction of the compound of formula[XXVI] with the compound of the formula[XXVII] in an organic solvent in the presence of a base such as sodium hydride.

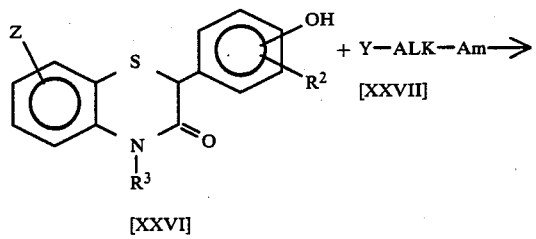

[XXVI]

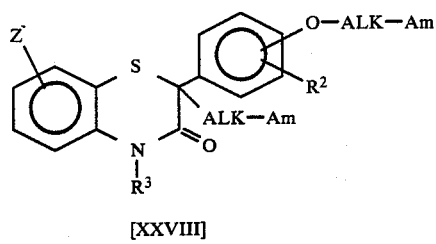

[XXVIII]

(F) In the previous reactions, when $R^1$, $R^2$ and/or $R^4$ are/is hydroxy, if necessary, acyl or tetrahydropyranyl group can be introduced by the known methods.

When $R^1$, $R^2$, and/or $R^4$ are/is primary or secondary amine, if necessary, the compound can be acylated by the known methods.

The acyl or tetrahydropyranyl group, if the group is used as protective group, can be removed by the known methods such as treatment with acid or alkali.

The compound of this invention can be converted into acid salts by the usual methods using inorganic or organic acids. Examples of pharmaceutically acceptable salts of the compounds are hydrochloric acid salt, sulfuric acid salt, phosphoric acid salt, lactic acid salt, maleic acid salt, fumaric acid salt, oxalic acid salt, citric acid salt, methanesulfonic acid salt, benzoic acid salt, p-toluenesulfonic acid salt, etc.

The compounds of this invention have stereoisomers because of the existence of one or more asymmetric carbon atoms, and these isomers are included in this invention.

BEST MODE TO MAKE THE INVENTION

Examples are shown below, and the compounds are listed in Table 1–7.

EXAMPLE 1

2-Chloro-3,4-dihydro-2-(4-hydroxyphenyl)-3-oxo-2H-1,4-benzothiazine (compound No. 1)

To a stirred suspension of 3,4-dihydro-2-(4-hydroxyphenyl)-3-oxo-2H-1,4-benzothiazine (25.7 g) in methylene chloride (220 ml), sulfuryl chloride (8.4 ml) is added under ice-cooling. The mixture is stirred for 2 hours at room temperature, and the separated crystals are collected by filtration to give 26.2 g (89.6%) of the compound.

mp 138°–158° C. (dec.).

IR (KBr, cm$^{-1}$, the same shall be applied hereinafter unless specified): 3216, 2908, 1654, 1594, 1577, 1509, 1476, 1356, 1217.

Following compounds are prepared by the similar method as in Example 1.

2-Chloro-3,4-dihydro-2-(4-hydroxyphenyl)-4-methyl-3-oxo-2H-1,4-benzothiazine (compound No. 2)

mp. 150°–162° C. (dec.).

IR: 3304, 1630, 1609, 1583, 1509, 1466, 1359, 1264, 1243, 1216.

2-Chloro-3,4-dihydro-2-(2-hydroxy-5-methoxyphenyl)-4-methyl-3-oxo-2H-1,4-benzothiazine (compound No. 3)

mp. 121°–128° C. (dec.).

IR: 3248, 1650, 1583, 1496, 1491, 1473, 1467, 1280, 1261, 1201, 1037, 750.

EXAMPLE 2

3,4-Dihydro-2-(2-hydroxy-5-methoxyphenyl)-2-methoxy-4-methyl-3-oxo-2H-1,4-benzothiazine (compound No. 6)

A mixture of 2-chloro-3,4-dihydro-2-(2-hydroxy-5-methoxyphenyl)-4-methyl-3-oxo-2H-1,4-benzothiazine (14.0 g, compound No. 3) and methanol (200 ml) is stirred for 2 hours at room temperature, and the separated crystals are collected by filtration to give 11.8 g (85.3%) of the titled compound.

mp. 135°–136.5° C.

IR: 3436, 1665, 1499, 1467, 1414, 1349, 1254, 1201, 1097, 1032, 838, 763.

Following compounds are prepared by the similar method as in Example 2.

3,4-Dihydro-2-(4-hydroxyphenyl)-2-methoxy-3-oxo-2H-1,4-benzothiazine (compound No. 4)

mp. 175°–177.5° C. (dec.)(ethyl acetate—acetone).
IR: 3228, 1665, 1593, 1583, 1510, 1434, 1356, 1282, 1263, 1215, 1165, 748.

3,4-Dihydro-2-(4-hydroxyphenyl)-2-methoxy-4-methyl-3-oxo-2H-1,4-benzothiazine (compound No. 5)

mp. 206°–208° C. (dec.).
IR: 3296, 1637, 1611, 1584, 1510, 1355, 1271, 1210.

EXAMPLE 3

3,4-Dihydro-2-(2-hydroxy-5-methoxyphenyl)-4-methyl-2-methylthio-3-oxo-2H-1,4-benzothiazine (compound No. 8)

2-Chloro-3,4-dihydro-2-(2-hydroxy-5-methoxyphenyl)-4-methyl-3-oxo-2H-1,4-benzothiazine (12.3 g, compound No. 3) is added to a mixture of 30% aqueous methyl mercaptan solution (26 ml) and tetrahydrofuran (50 ml). The mixture is stirred for 1.5 hours at room temperature and concentrated in vacuo. The separated crystals are collected by filtration to give 10.0 g (78.3%) of the titled compound.

mp. 167°–168.5° C. (dec.).
IR: 3300, 1647, 1584, 1281, 1225.

Following compound is prepared by the similar method as in Example 3.

3,4-Dihydro-2-(4-hydroxyphenyl)-4-methyl-2-methylthio-3-oxo-2H-1,4-benzothiazine (compound No. 7)

mp. 199.5°–201.5° C.
IR: 3372, 1637, 1608, 1582, 1509, 1475, 1434, 1356, 1264, 1222, 758.

EXAMPLE 4

3,4-dihydro-2-(4-hydroxyphenyl)-4-methyl-3-oxo-2-phenylthio-2H-1,4-benzothiazine (compound No. 9)

To a stirred solution of thiophenol (6.7 ml) in tetrahydrofuran (15 ml), 2-chloro-3,4-dihydro-2-(4-hydroxyphenyl)-4-methyl-3-oxo-2H-1,4-benzothiazine (4.0 g, compound No. 2) is added. The mixture is stirred for 3 hours at room temperature, and then concentrated in vacuo. The residue is purified by silica gel column chromatography to give 4.5 g (90.0%) of the titled compound.

mp. 181°–183° C. (dec.)(benzene-ethyl acetate).
IR: 3156, 1654, 1606, 1581, 1466, 1437, 1344, 1273, 1250, 1236, 744.

EXAMPLE 5

2-Cyano-3,4-dihydro-2-(4-hydroxyphenyl)-4-methyl-3-oxo-2H-1,4-benzothiazine (compound No. 10)

To a stirred solution of 2-chloro-3,4-dihydro-2-(4-hydroxyphenyl)-4-methyl-3-oxo-2H-1,4-benzothiazine (10.0 g, compound No. 2) in dimethylsulfoxide (100 ml), sodium cyanide (8.0 g) is added. The mixture is stirred for 2 hours at room temperature, and poured into a mixture of ethyl acetate and water. The organic layer is washed with water, dried over anhydrous sodium sulfate, and concentrated in vacuo to give 6.9 g (71.0%) of the titled compound.

mp. 200°–206° C. (dec.).
IR: 3312, 2210, 1654, 1610, 1585, 1513, 1442, 1362, 1268, 1224, 1205, 750.

EXAMPLE 6

3,4-Dihydro-2-hydroxy-2-(4-hydroxyphenyl)-4-methyl-3-oxo-2H-1,4-benzothiazine (compound No. 11)

2-Chloro-3,4-dihydro-2-(4-hydroxyphenyl)-4-methyl-3-oxo-2H-1,4-benzothiazine (0.1 g, compound No. 2) is dissolved in a mixture of tetrahydrofuran (2 ml) and water (1 ml), and the solution is standed overnight at room temperature. The mixture is poured into a mixture of ethyl acetate and water. The organic layer is dried over anhydrous sodium sulfate, and concentrated in vacuo to give 0.1 g (quant. yield) of the titled compound as amorphous powder.

IR: 3308, 1635, 1610, 1583, 1509, 1466, 1442, 1356, 1261, 1220, 1171.

EXAMPLE 7

3,4-Dihydro-2,4-dimethyl-2-(4-hydroxyphenyl)-3-oxo-2H-1,4-benzothiazine (compound No. 13)

To a stirred solution of 3,4-dihydro-2,4-dimethyl-3-oxo-2H-1,4-benzothiazine (4.8 g) in methylene chloride (25 ml), sulfuryl chloride (3.5 g) is added under ice-cooling. The mixture is stirred for 30 minutes, and added into a solution of phenol (2.4 g) and aluminum chloride (3.3 g) in methylene chloride (20 ml) with stirring under ice-cooling. The mixture is stirred for 1 hour under ice-cooling, and washed with water, saturated aqueous sodium bicarbonate solution and saturated aqueous sodium chloride solution. The solution is dried over anhydrous sodium sulfate and concentrated in vacuo. A mixture of benzene and n-hexane (1:1) is added to the residue and the separated crystals are collected by filtration to give 6.4 g (90.2%) of the titled compound.

mp. 158.5°–160° C.
IR: 3260, 1624, 1584, 1509, 1437, 1360, 1265, 1221, 1205, 1173, 830, 750.

Following compound is prepared by the similar method as in Example 7.

3,4-Dihydro-2,4-dimethyl-2-(2-hydroxy-5-methoxyphenyl)-3-oxo-2H-1,4-benzothiazine (compound No. 12)

mp. 175.5°–176.5° C.
IR: 3216, 1629, 1584, 1499, 1465, 1412, 1351, 1275, 1262, 1198, 1036, 806, 742.

EXAMPLE 8

3,4-Dihydro-4,7-dimethyl-2-(4-hydroxyphenyl)-3-oxo-2H-1,4-benzothiazine (compound No. 15)

To a stirred solution of 3,4-dihydro-4,7-dimethyl-3-oxo-2H-1,4-benzothiazine (11.0 g) in methylene chloride (50 ml), sulfuryl chloride (4.8 ml) is added under ice-cooling. After the addition, the mixture is stirred for 15 minutes under ice-cooling. Phenol (7.0 g) is added to the mixture, and the mixture is stirred for 45 minutes and concentrated in vacuo. Ether is added to the residue and the separated crystals are collected by filtration to give 11.3 g (69.4%) of the titled compound.

mp. 186°–187° C. (ethyl acetate).
IR: 3372, 1635, 1593, 1491, 1444, 1361, 1264, 1213, 1131, 811.

Following compounds are prepared by the similar method as in Example 8.

3,4-Dihydro-4,7-dimethyl-2-(2-hydroxy-5-methoxyphenyl)-3-oxo-2H-1,4-benzothiazine (compound No. 14)

mp. 163°–164° C.
IR: 3020, 1615, 1492, 1419, 1363, 1266, 1205, 1137, 815.

7-Chloro-3,4-dihydro-2-(2-hydroxy-5-methoxyphenyl)-4-methyl-3-oxo-2H-1,4-benzothiazine (compound No. 16)

mp. 175°–178° C.
IR: 1624, 1476, 1424, 1267, 1208, 816.

7-Chloro-3,4-dihydro-2-(4-hydroxyphenyl)-4-methyl-3-oxo-2H-1,4-benzothiazine (compound No. 17)

mp. 196°–199° C.
IR: 3336, 1636, 1511, 1472, 1356, 1225, 807.

EXAMPLE 9

2-(4-Acetoxyphenyl)-3,4-dihydro-2-methoxy-4-methyl-3-oxo-2H-1,4-benzothiazine (compound No. 20)

3,4-Dihydro-2-(4-hydroxyphenyl)-2-methoxy-4-methyl-3-oxo-2H-1,4-benzothiazine (0.2 g, compound No. 5) is dissolved in a mixture of acetic anhydride (2 ml) and pyridine (5 ml). The mixture is standed for 3 hours at room temperature, and then poured into a mixture of benzene and dilute hydrochloric acid. The organic layer is washed with water, dried over anhydrous sodium sulfate and concentrated in vacuo. The separated crystals are collected by filtration to give 0.1 g (52.7%) of the titled compound.
mp. 144°–145.5° C.
IR: 1753, 1665, 1353, 1198, 1167, 757.

Following compound is prepared by the similar method as in Example 9.

2-(4-Acetoxyphenyl)-3,4-dihydro-4-methyl-2-methylamino-3-oxo-2H-1,4-benzothiazine (compound No. 68)

mp. 131.5°–133.5° C.
IR: 3356, 1753, 1655, 1499, 1467, 1441, 1429, 1419, 1277, 1259, 1193, 1167

EXAMPLE 10

2-Cyano-3,4-dihydro-2-[4-(2,3-epoxypropoxy)phenyl]-4-methyl-3-oxo-2H-1,4-benzothiazine (compound No. 23)

To a stirred suspension of 60% sodium hydride (0.7 g) in anhydrous dimethylformamide (5 ml), 2-cyano-3,4-dihydro-2-(4-hydroxyphenyl)-4-methyl-3-oxo-2H-1,4-benzothiazine (5.0 g, compound No. 10) dissolved in anhydrous dimethylformamide (15 ml) is added under nitrogen atmosphere and ice-cooling, and the mixture is stirred for 7 minutes at room temperature. Epichlorohydrin(2.6 ml) is added to the reaction mixture, and the mixture is stirred for 1 hour at 65°–75° C. The mixture is poured into a mixture of ethyl acetate and water. The organic layer is washed with saturated aqueous sodium chloride solution, dried over anhydrous sodium sulfate and concentrated in vacuo. The residue is purified by silica gel column chromatography to give 3.2 g (54.5%) of the titled compound.
mp. 135.5°–139° C.
IR: 2209, 1664, 1603, 1465, 1457, 1346, 1301, 1251, 747.

EXAMPLE 11

2-[4-(3-tert-Butylamino-2-hydroxypropoxy)phenyl]-2-cyano-3,4-dihydro-4-methyl-3-oxo-2H-1,4-benzothiazine (compound No. 24)

To a stirred suspension of 2-cyano-3,4-dihydro-2-[4-(2,3-epoxypropoxy)phenyl]-4-methyl-3-oxo-2H-1,4-benzothiazine (1.2 g, compound No. 23) in ethanol (15 ml), tert-butylamine (3.6 ml) is added. The mixture is refluxed for 1.5 hours, and concentrated in vacuo to give 1.3 g (74.8%) of the titled compound.
mp. 159.5°–160.5° C. (ethyl acetate-methanol).
IR: 3300, 2920, 2237, 1664, 1602, 1582, 1502, 1464, 1355, 1277, 1250, 754.

Following compound is prepared by the similar method as in Example 11.

3,4-Dihydro-2-[2-[2-hydroxy-3-(4-phenacyl-1-piperazino)propoxy]-5-methoxyphenyl]-2-methoxy-4-methyl-3-oxo-2H-1,4-benzothiazine hydrochloride (compound No. 25)

IR: 3008, 1660, 1587, 1228, 1201, 1035, 751.

EXAMPLE 12

2-(3-Chloropropyl)-3,4-dihydro-2-(2,5-dimethoxyphenyl)-4-methyl-3-oxo-2H-1,4-benzothiazine (compound No. 27)

To a stirred suspension of 60% sodium hydride (0.7 g) in anhydrous dimethylformamide (10 ml), 3,4-dihydro-2-(2,5-dimethoxyphenyl)-4-methyl-3-oxo-2H-1,4-benzothiazine (5.0 g) dissolved in anhydrous dimethylformamide (15 ml) is added under nitrogen atmosphere and ice-cooling, and the mixture is stirred for 20 minutes at room temperature. 1-Bromo-3-chloropropane (3.0 g) dissolved in dimethylformamide (5 ml) is added to a reaction mixture, and the mixture is stirred for 1.5 hours at 50° C. The mixture is poured into a mixture of ethyl acetate and water. The organic layer is washed with saturated aqueous sodium chloride solution, dried over anhydrous sodium sulfate and concentrated in vacuo. The residue is purified by silica gel column chromatography to give 5.4 g (86.9%) of the titled compound as an oily form.
IR (neat, cm$^{-1}$): 1665, 1584, 1493, 1343, 1274, 1255, 1222, 1042, 750.

Following compound is prepared by the similar method as in Example 12.

2-(3-Chloropropyl)-3,4-dihydro-2-(3,4-dimethoxyphenyl)-4-methyl-3-oxo-2H-1,4-benzothiazine (compound No. 28)

IR (neat, cm$^{-1}$): 1656, 1585, 1508, 1409, 1348, 1256, 1238, 1142, 1025, 749.

EXAMPLE 13

2-(4-Bromobutyl)-3,4-dihydro-2-(3,4-dimethoxyphenyl)-4-methyl-3-oxo-2H-1,4-benzothiazine (compound No. 32)

3,4-Dihydro-2-(3,4-dimethoxyphenyl)-4-methyl-3-oxo-2H-1,4-benzothiazine (5.0 g) and 1,4-dibromobutane (10.3 g) are treated by the similar method as in Example 12 to give 4.8 g (66.9%) of the titled compound.
IR (neat, cm$^{-1}$): 1657, 1585, 1479, 1462, 1348, 1257, 1236, 1145, 1025, 750.

Following compounds are prepared by the similar method as in Example 13.

2-(4-Bromobutyl)-2-[5-methoxy-2-(tetrahydropyran-2-yloxy)phenyl]-4-methyl-3-oxo-2H-1,4-benzothiazine (compound No. 34)

IR (neat, cm$^{-1}$): 2936, 1671, 1585, 1492, 1466, 1441, 1343, 1279, 1255, 1218, 1200, 1036.

2-(4-Bromobutyl)-3,4-dihydro-2-(4-methoxyphenyl)-4-methyl-3-oxo-2H-1,4-benzothiazine (compound No. 30)

IR (neat, cm$^{-1}$): 2938, 1660, 1585, 1257, 1027.

EXAMPLE 14

3,4-Dihydro-2-(2-hydroxy-5-methoxyphenyl)-4-methyl-2-(4-methylthiobutyl)-3-oxo-2H-1,4-benzothiazine (compound No. 35)

To a stirred solution of 2-(4-bromobutyl)-2-[5-methoxy-2-(tetrahydropyran-2-yloxy)phenyl]-4-methyl-3-oxo-2H-1,4-benzothiazine (4.9 g, compound No. 34) in ethanol (25 ml), 20–25% aqueous sodium methyl mercaptan solution (16.6 ml) is added. Ethanol (15 ml) and tetrahydrofuran (20 ml) are added to the mixture. The mixture is stirred for 45 minutes at room temperature, and concentrated in vacuo. 2N Hydrochloric acid (50 ml), tetrahydrofuran (25 ml) and ethanol (25 ml) are added to the residue dissolved in tetrahydrofuran (50 ml), and the mixture is stirred for 45 minutes at room temperature. The reaction mixture is poured into a mixture of ethyl acetate and water. The organic layer is washed with saturated aqueous sodium bicarbonate solution, dried over anhydrous sodium sulfate and concentrated in vacuo. The separated crystals are collected by filtration to give 3.0 g (77.3%) of the titled compound.

mp. 147.5°–150.5° C.
IR: 3204, 2912, 1637, 1583, 1501, 1457, 1443, 1413, 1348, 1279, 1260, 1196.

EXAMPLE 15

2-[2-(3-Chloropropoxy)-5-methoxyphenyl]-3,4-dihydro-4-methyl-2-methylthio-3-oxo-2H-1,4-benzothiazine (compound No. 41)

To a stirred suspension of 60% sodium hydride (0.5 g) in dimethylformamide (10 ml), 3,4-dihydro-2-(2-hydroxy-5-methoxyphenyl)-4-methyl-2-methylthio-3-oxo-2H-1,4-benzothiazine (3.5 g, compound No. 8) dissolved in dimethylformamide (5 ml) is added under nitrogen atmosphere and ice-cooling, and the mixture is stirred for 10 minutes at room temperature. 1-Bromo-3-chloropropane (1.9 g) is added to the reaction mixture, and the mixture is stirred for 1 hour at 50°–60° C. The mixture is poured into a mixture of ethyl acetate and water. The organic layer is washed with saturated aqueous sodium chloride solution, dried over anhydrous sodium sulfate and concentrated in vacuo. The separated crystals are collected by filtration to give 4.0 g (93.4%) of the titled compound.

mp. 135°–137° C.
IR: 1664, 1494, 1474, 1452, 1345, 1270, 1254, 1221, 1044, 750.

Following compounds are prepared by the similar method as in Example 15.

2-[4-(3-Chloropropoxy)phenyl]-3,4-dihydro-2-methoxy-3-oxo-2H-1,4-benzothiazine (compound No. 38)

IR: 1673, 1606, 1582, 1509, 1479, 1350, 1245, 1218, 1176, 1072, 748.

2-[2-(3-Chloropropoxy)-5-methoxyphenyl]-3,4-dihydro-2-methoxy-4-methyl-3-oxo-2H-1,4-benzothiazine (compound No. 39)

IR (neat, cm$^{-1}$): 1671, 1585, 1498, 1479, 1443, 1278, 1263, 1223, 1038, 751, 680.

2-[2-(3-Chloropropoxy)-5-methoxyphenyl]-3,4-dihydro-4-methyl-2-(4-methylthiobutyl)-3-oxo-2H-1,4-benzothiazine (compound No. 44)

IR (neat, cm$^{-1}$): 2920, 1666, 1585, 1493, 1479, 1465, 1342, 1278, 1255, 1220, 1040, 750.

EXAMPLE 16

2-[2-(4-Bromobutoxy)-5-methoxyphenyl]-3,4-dihydro-4-methyl-2-methylthio-3-oxo-2H-1,4-benzothiazine (compound No. 43)

3,4-Dihydro-2-(2-hydroxy-5-methoxyphenyl)-4-methyl-2-methylthio-3-oxo-2H-1,4-benzothiazine (3.5 g, compound No. 8) and 1,4-dibromobutane (3.6 ml) are treated by the similar method as in Example 15 to give 3.9 g (80.0%) of the titled compound.

mp. 101.5°–103° C.
IR: 1671, 1493, 1438, 1341, 1278, 1251, 1220, 1043.

Following compounds are prepared by the similar method as in Example 16.

2-[2-(4-Bromobutoxy)-5-methoxyphenyl]-3,4-dihydro-2-methoxy-4-methyl-3-oxo-2H-1,4-benzothiazine (compound No. 40)

IR (neat, cm$^{-1}$): 1668, 1585, 1497, 1476, 1469, 1351, 1278, 1261, 1222, 1039, 751, 680.

2-[4-(4-Bromobutoxy)phenyl]-3,4-dihydro-4-methyl-2-methylthio-3-oxo-2H-1,4-benzothiazine (compound No. 42)

mp. 85°–86.5° C.
IR: 2916, 1661, 1599, 1501, 1478, 1459, 1445, 1438, 1338, 1245.

2-(N-Acetylmethylamino)-2-[2-(4-bromobutoxy)-5-methoxyphenyl]-3,4-dihydro-4-methyl-3-oxo-2H-1,4-benzothiazine (compound No. 73)

mp. 124°–127° C.
IR: 1663, 1582, 1493, 1474, 1419, 1278, 1250, 1222, 1146, 1034, 1023, 754.

2-[4-(4-Bromobutoxy)phenyl]-3,4-dihydro-2-(3-dimethylaminopropyl)-4-methyl-3-oxo-2H-1,4-benzothiazine hydrochloride (compound No. 92)

IR: 3396, 2652, 1647, 1605, 1582, 1503, 1466, 1349, 1244, 1177, 749.

2-[2-(4-Bromobutoxy)-5-methoxyphenyl]-3,4-dihydro-2,4-dimethyl-3-oxo-2H-1,4-benzothiazine (compound No. 46)

mp. 78°–80° C.
IR: 2912, 1662, 1583, 1457, 1339, 1273, 1256, 1217, 1036, 748.

2-[4-(4-Bromobutoxy)phenyl]-3,4-dihydro-2,4-dimethyl-3-oxo-2H-1,4-benzothiazine (compound No. 49)

IR: 3416, 2924, 1660, 1606, 1586, 1508, 1474, 1443, 1348, 1246, 1180, 750.

2-[2-(4-Bromobutoxy)-5-methoxyphenyl]-3,4-dihydro-4,7-dimethyl-3-oxo-2H-1,4-benzothiazine (compound No. 52)

mp. 102°–104° C.
IR: 1654, 1492, 1466, 1356, 1305, 1239, 1219, 1039, 807.

2-[4-(4-Bromobutoxy)phenyl]-3,4-dihydro-4,7-dimethyl-3-oxo-2H-1,4-benzothiazine (compound No. 55)

mp. 75°–76° C. (benzene—n-hexane).
IR: 1659, 1607, 1509, 1494, 1469, 1354, 1303, 1245, 1176, 1134, 808, 749.

2-[2-(4-Bromobutoxy)-5-methoxyphenyl]-7-chloro-3,4-dihydro-4-methyl-3-oxo-2H-1,4-benzothiazine (compound No. 58)

mp. 106°–107° C. (ethyl acetate—n-hexane).
IR: 1653, 1500, 1467, 1353, 1307, 1241, 1220, 1203, 1042, 806.

2-[4-(4-Bromobutoxy)phenyl]-7-chloro-3,4-dihydro-4-methyl-3-oxo-2H-1,4-benzothiazine (compound No. 61)

mp. 70°–72° C. (ethyl acetate—isopropyl ether—n-hexane).
IR: 1651, 1465, 1236, 1119, 1106, 804.

2-[2-(3-Bromopropoxy)-5-methoxyphenyl]-3,4-dihydro-2,4-dimethyl-3-oxo-2H-1,4-benzothiazine (compound No. 45)

mp. 107°–108.5° C.
IR: 3388, 2924, 1662, 1493, 1477, 1451, 1344, 1293, 1272, 1259, 1215, 1036, 801, 750.

2-[4-(3-Bromopropoxy)phenyl]-3,4-dihydro-4-methyl-2-(1-methylethyl)-3-oxo-2H-1,4-benzothiazine (compound No. 65)

IR: 2925, 1660, 1583, 1246, 1223, 1035, 750.

2-[4-(5-Bromopentyloxy)phenyl]-3,4-dihydro-4,7-dimethyl-3-oxo-2H-1,4-benzothiazine (compound No. 56)

mp. 81°–82° C. (benzene).
IR: 2896, 2860, 1652, 1606, 1492, 1457, 1351, 1241, 1177, 797.

2-[2-(5-Bromopentyloxy)-5-methoxyphenyl]-3,4-dihydro-2,4-dimethyl-3-oxo-2H-1,4-benzothiazine (compound No. 47)

mp. 78°–80° C.
IR: 2928, 1668, 1585, 1492, 1467, 1405, 1395, 1338, 1274, 1253, 1215, 1038, 750.

2-[4-(5-Bromopentyloxy)phenyl]-3,4-dihydro-2,4-dimethyl-3-oxo-2H-1,4-benzothiazine compound No. 50)

IR: 2928, 1659, 1606, 1586, 1508, 1473, 1444, 1348, 1282, 1246, 1180, 1040.

2-[2-(5-Bromopentyloxy)-5-methoxyphenyl]-3,4-dihydro-4,7-dimethyl-3-oxo-2H-1,4-benzothiazine (compound No. 53)

mp. 62°–64° C.

IR: 1654, 1492, 1463, 1356, 1303, 1239, 1218, 1038, 810.

2-[2-(5-Bromopentyloxy)-5-methoxyphenyl]-7-chloro-3,4-dihydro-4-methyl-3-oxo-2H-1,4-benzothiazine (compound No. 59)

mp. 105°–106° C. (ethyl acetate—n-hexane).
IR: 1654, 1497, 1472, 1348, 1269, 1240, 1204, 798.

2-[4-(5-Bromopentyloxy)phenyl]-7-chloro-3,4-dihydro-4-methyl-3-oxo-2H-1,4-benzothiazine (compound No. 62)

mp. 66°–68° C. (ethyl acetate—isopropyl ether).
IR: 1654, 1465, 1299, 1246, 1238, 803.

EXAMPLE 17

3,4-Dihydro-2-(4-hydroxyphenyl)-4-methyl-2-methylamino-3-oxo-2H-1,4-benzothiazine (compound No. 66)

To a stirred suspension of 2-chloro-3,4-dihydro-2-(4-hydroxyphenyl)-4-methyl-3-oxo-2H-1,4-benzothiazine (11.5 g, compound No. 2) in tetrahydrofuran (40 ml), 40% aqueous methylamine solution (14.6 ml) is added. The mixture is stirred for 2 hours at room temperature, and poured into a mixture of ethyl acetate and water. The organic layer is washed with saturated aqueous sodium chloride solution, dried over anhydrous sodium sulfate and concentrated in vacuo to give 10.1 g (89.8%) of the titled compound.

mp. 165°–168° C. (dec.).
IR: 3280, 2932, 1647, 1628, 1604, 1581, 1466, 1457, 1352, 1271, 1259, 754.

Following compound is prepared by the similar method as in Example 17.

3,4-Dihydro-2-(2-hydroxy-5-methoxyphenyl)-4-methyl-2-methylamino-3-oxo-2H-1,4-benzothiazine (compound No. 67)

mp. 183.5°–185° C. (dec.).
IR: 3308, 2940, 1650, 1615, 1582, 1458, 1449, 1296, 1266, 1236, 1212, 1030.

EXAMPLE 18

2-(4-Acetoxyphenyl)-2-(N-acetylmethylamino)-3,4-dihydro-4-methyl-3-oxo-2H-1,4-benzothiazine (compound No. 70)

To a stirred suspension of 3,4-dihydro-2-(4-hydroxyphenyl)-4-methyl-2-methylamino-3-oxo-2H-1,4-benzothiazine (3.0 g, compound No. 66) in acetic anhydride (14.3 ml), fused sodium acetate (3.3 g) is added. The mixture is stirred for 3.5 hours at 85° C. and then poured into a mixture of ethyl acetate and saturated aqueous sodium bicarbonate solution. The separated crystals are collected by filtration to give 3.3 g (85.7%) of the title compound.

mp. 182.5°–184° C.
IR: 3536, 3452, 1753, 1653, 1472, 1378, 1366, 1341, 1196, 1169.

Following compound is prepared by the similar method as in Example 18.

2-(2-Acetoxy-5-methoxyphenyl)-2-(N-acetylmethylamino)-3,4-dihydro-4-methyl-3-oxo-2H-1,4-benzothiazine (compound No. 72)

mp. 150.5°–152° C.
IR: 1759, 1654, 1611, 1583, 1478, 1315, 1291, 1281, 1250, 1041, 1020, 759.

EXAMPLE 19

2-(N-Acetylmethylamino)-3,4-dihydro-2-(4-hydroxyphenyl)-4-methyl-3-oxo-2H-1,4-benzothiazine (compound No. 69)

To a stirred suspension of 2-(4-acetoxyphenyl)-2-(N-acetylmethylamino)-3,4-dihydro-4-methyl-3-oxo-2H-1,4-benzothiazine (3.2 g, compound No. 70) in tetrahydrofuran (20 ml), a mixture of 2N sodium hydroxide (20.8 ml) and tetrahydrofuran (20 ml) is added. The mixture is stirred for 20 minutes at room temperature and poured into 2N hydrochloric acid. The separated crystals are collected by filtration to give 2.6 g (91.6%) of the titled compound.

mp. 288°–293° C. (dec.).
IR: 3288, 1658, 1609, 1590, 1582, 1510, 1474, 1438, 1376, 1341, 1264.

Following compound is prepared by the similar method as in Example 19.

2-(N-Acetylmethylamino)-3,4-dihydro-2-(2-hydroxy-5-methoxyphenyl)-4-methyl-3-oxo-2H-1,4-benzothiazine (compound No. 71)

mp. 164°–167.5° C. (isopropyl ether—ethyl acetate).
IR: 3408, 3312, 1665, 1625, 1581, 1491, 1481, 1419, 1349, 1282, 1228, 753.

EXAMPLE 20

3,4-Dihydro-2-(3-dimethylaminopropyl)-4-methyl-3-oxo-2-[4-(tetrahydropyran-2-yloxy)phenyl]-2H-1,4-benzothiazine (compound No. 76)

To a stirred suspension of 60% sodium hydride (3.1 g) in dimethylformamide (30 ml), 3,4-dihydro-4-methyl-3-oxo-2-[4-(tetrahydropyran-2-yloxy)phenyl]-2H-1,4-benzothiazine (25.0 g) dissolved in dimethylformamide (60 ml) is added under nitrogen atmosphere, and the mixture is stirred for 30 minutes. A solution of 3-dimethylaminopropyl chloride in dimethylformamide [prepared by mixing of 3-dimethylaminopropyl chloride hydrochloride (13.3 g) and triethylamine (11.8 ml) in dimethylformamide (50 ml) and followed by filtration to remove precipitate] is added to the reaction mixture, and the mixture is stirred for 1 hour at 65°–75° C. The mixture is poured into water and extracted with ethyl acetate. The organic layer is washed with saturated aqueous sodium chloride solution, dried over anhydrous sodium sulfate, and concentrated in vacuo to give 25.1 g (81.0%) of the titled compound.

mp. 98.5°–101° C.
IR: 1655, 1502, 1344, 1256, 1236, 1176, 1110, 1034, 960.

EXAMPLE 21

3,4-Dihydro-2-(3-dimethylaminopropyl)-2-(4-hydroxyphenyl)-4-methyl-3-oxo-2H-1,4-benzothiazine (compound No. 75)

A mixture of 3,4-dihydro-2-(3-dimethylaminopropyl)-4-methyl-3-oxo-2-[4-(tetrahydropyran-2-yloxy)phenyl-2H-1,4-benzothiazine (24.1 g, compound No. 76) and 1N hydrochloric acid (100 ml) is stirred for 1 hour. The reaction mixture is washed with ether, and the aqueous layer is neutralized with 2N sodium hydroxide. The separated crystals are collected by filtration to give 19.3 g (99.0%) of the titled compound.

mp. 185°–187° C.

IR: 1654, 1607, 1583, 1500, 1466, 1347, 1276, 1263, 1254, 1173, 829, 745.

EXAMPLE 22

3,4-Dihydro-2-(3,4-dimethoxyphenyl)-2-(3-dimethylaminopropyl)-4-methyl-3-oxo-2H-1,4-benzothiazine oxalate (compound No. 79)

To a stirred suspension of 60% sodium hydride (0.3 g) in dimethylformamide (10 ml), 3,4-dihydro-2-(3,4-dimethoxyphenyl)-4-methyl-3-oxo-2H-1,4-benzothiazine (2.0 g) dissolved in dimethylformamide (10 ml) is added under nitrogen atmosphere and ice-cooling, and the mixture is stirred for 15 minutes at room temperature. A solution of 3-dimethylaminopropyl chloride in dimethylformamide [prepared by mixing of 3-dimethylaminopropyl chloride hydrochloride (1.1 g) and triethylamine (1.0 ml) in dimethylformamide (10 ml) and followed by a filtration to remove precipitate] is added to the reaction mixture, and the mixture is stirred for 2 hours at 50°–60° C. The mixture is poured into a mixture of ethyl acetate and hydrochloric acid, and the aqueous layer is extracted with chloroform. The organic layer is concentrated in vacuo, and ethyl acetate and 2N sodium hydroxide are added to the residual oil. The organic layer is washed with saturated aqueous sodium chloride solution, dried over anhydrous sodium sulfate and concentrated in vacuo. The residue is purified by silica gel column chromatography. The product is dissolved in ethyl acetate, and to the solution oxalic acid in ethyl acetate is added to give 1.6 g (50.5%) of the titled compound.

mp. 136°–138° C. (ethyl acetate—ethanol).
IR: 3404, 2660, 1715, 1698, 1633, 1583, 1507, 1256, 1233, 1139, 1109, 717.

Following compounds are prepared by the similar method as in Example 22.

3,4-Dihydro-2-3-dimethylaminopropyl)-2-(4-methoxyphenyl)-4-methyl-3-oxo-2H-1,4-benzothiazine oxalate (compound No. 77)

mp. 191°–192° C. (dec.)(ethanol—water).
IR: 3400, 2680, 1699, 1653, 1607, 1577, 1503, 1457, 1350, 1245, 1173, 1027.

3,4-Dihydro-2-(2,5-dimethoxyphenyl)-2-(3-dimethylaminopropyl)-4-methyl-3-oxo-2H-1,4-benzothiazine oxalate (compound No. 78)

mp. 158°–160° C. (ethyl acetate—ethanol).
IR: 3412, 2640, 1716, 1699, 1651, 1582, 1460, 1275, 1218, 1110, 1036, 717.

3,4-Dihydro-2-(2,5-dimethoxyphenyl)-4-methyl-2-[3-(N-methylcyclohexylamino)propyl]-3-oxo-2H-1,4-benzothiazine oxalate (compound No. 80)

mp. 159°–161° C. (ethyl acetate—ethanol).
IR: 3420, 2576, 1716, 1653, 1583, 1464, 1400, 1342, 1275, 1217, 1037, 718.

EXAMPLE 23

3,4-Dihydro-2,4-dimethyl-2-[4-(3-dimethylaminopropoxy)phenyl]-3-oxo-2H-1,4-benzothiazine fumarate (compound No. 107)

To a stirred suspension of 60% sodium hydride (0.4 g) in dimethylformamide, 3,4-dihydro-2-[4-(3-dimethylaminopropoxyl)phenyl-4-methyl-3-oxo-2H-1,4-benzothiazine (3.6 g) dissolved in dimethylformamide (10 ml) is added under nitrogen atmosphere and ice-cooling, and the mixture is stirred for 20 minutes at room temperature. Methyl iodide (0.6 ml) in anhydrous dimethylformamide (5 ml) is added to the reaction mixture, and the mixture is stirred for 1.5 hours at room temperature. The mixture is poured into a mixture of ethyl acetate and water. The organic layer is washed with saturated aqueous sodium chloride solution, dried over anhydrous sodium sulfate and concentrated in vacuo. The residue is purified by silica gel column chromatography. The product is dissolved in ethyl acetate, and to the solution fumaric acid in methanol is added and the separated cryatals are collected by filtration to give 0.5 g (10.3%) of the titled compound.

mp. 158.5–160.5° C. (isopropanol—n-hexane).
IR: 3392, 2912, 2640, 1649, 1505, 1468, 1346, 1245, 1177, 1037, 979, 745, 644.

EXAMPLE 24

3,4-Dihydro-2-(3,4-dimethoxyphenyl)-4-methyl-2-[3-(N-methyl-3,4,5-trimethoxyphenethylamino)propyl[-3-oxo-2H-1,4-benzothiazine oxalate (compound No. 82)

To a stirred solution of 2-(3-chloropropyl)-3,4-dihydro-2-(3,4-dimethoxyphenyl)-4-methyl-3-oxo-2H-1,4-benzothiazine (1.5 g, compound No. 28) in acetone(20 ml), sodium iodide (0.6 g) is added, and the mixture is refluxed for 1 hour. The reaction mixture is filtered and the filtrate is concentrated in vacuo. The residue is dissolved in dimethylformamide (20 ml), and to the solution sodium carbonate (0.8 g) and N-methyl-3,4,5-trimethoxyphenethylamine (1.3 g) are added, and the mixture is stirred for 2 hours at 80°–90° C. The mixture is poured into a mixture of chloroform and 1N hydrochloric acid, and the organic layer is concentrated in vacuo. Ethyl acetate and 2N sodium hydroxide are added to the residual oil, and the organic layer is washed with saturated aqueous sodium chloride solution, dried over anhydrous sodium sulfate and concentrated in vacuo. The residue is purified by silica gel column chromatography. The product is dissolved in ethyl acetate, and to the solution of oxalic acid in ethyl acetate is added and the separated crystals are collected by filtration to give 1.8 g (70.1%) of the titled compound.

mp. 175.5°–177° C. (ethyl acetate).
IR: 3408, 2576, 1718, 1647, 1586, 1509, 1253, 1235, 1181, 1115, 1016, 752.

Following compounds are prepared by the similar method as in Example 24.

3,4-Dihydro-2-(2,5-dimethoxyphenyl)-4-methyl-2-[3-(N-methyl-3,4,5-trimethoxyphenethylamino)propyl[-3-oxo-2H-1,4-benzothiazine oxalate (compound No. 83)

mp. 163°–165° C. (ethyl acetate).
IR: 3420, 2572, 1715, 1653, 1585, 1491, 1276, 1221, 1178, 1118, 1037.

3,4-Dihydro-2-(3,4-dimethoxyphenyl)-4-methyl-2-[3-[N-methyl-2-(3,4-methylenedioxyphenoxy)ethylamino]propyl]-3-oxo-2H-1,4-benzothiazine oxalate (compound No. 84)

mp. 128°–130° C. (ethyl acetate—ethanol).
IR: 3392, 1718, 1647, 1583, 1476, 1407, 1345, 1254, 1183, 1139, 1022.

3,4-Dihydro-2-(3,4-dimethoxyphenyl)-2-[3-[4-(4-fluorobenzoyl)piperidino]propyl]-4-methyl-3-oxo-2H-1,4-benzothiazine oxalate (compound No. 93)

IR: 1654, 1652, 1580, 1275, 1250, 1075, 1043, 750.

3,4-Dihydro-2-[3-[4-(3,4-dimethoxyphenethyl)-piperazino]propyl]-2-(2,5-dimethoxyphenyl)-4-methyl-3-oxo-2H-1,4-benzothiazine dioxalate (compound No. 96)

IR: 3024, 2987, 1658, 1588, 1252, 1077, 1025.

3,4-Dihydro-2-(3,4-dimethoxyphenyl)-4-methyl-3-oxo-2-[3-[4-(3,4,5-trimethoxyphenethyl)piperazino]propyl]-2H-1,4-benzothiazine dioxalate (compound No. 97)

IR: 1657, 1499, 1273, 1222, 1034, 753.

EXAMPLE 25

3,4-Dihydro-2-(3,4-dimethoxyphenyl)-4-methyl-2-[4-(N-methyl-3,4,5-trimethoxyphenethylamino)butyl]-3-oxo-2H-1,4-benzothiazine oxalate (compound No. 88)

To a stirred solution of 2-(4-bromobutyl)-3,4-dihydro-2-(3,4-dimethoxyphenyl)-4-methyl-3-oxo-2H-1,4-benzothiazine (1.5 g, compound No. 32) in dimethylformamide (20 ml), sodium carbonate (0.7 g) and N-methyl-3,4,5-trimethoxyphenethylamine (1.1 g) are added, and the mixture is stirred for 1 hour at 80°–90° C. The mixture is poured into a mixture of chloroform and 1N hydrochloric acid, and the organic layer is concentrated in vacuo. The residue is treated by the similar method as in Example 24 to give 1.5 g (65.8%) of the titled compound.

mp. 144°–146° C. (ethanol).
IR: 3420, 2580, 1717, 1654, 1585, 1508, 1457, 1337, 1255, 1236, 1119, 1020.

Following compounds are prepared by the similar method as in Example 25.

3,4-Dihydro-2-(3,4-dimethoxyphenyl)-2-[4-[4-(α-hydroxybenzyl)piperidino]butyl]-4-methyl-3-oxo-2H-1,4-benzothiazine hydrochloride (compound No. 94)

IR: 3024, 2928, 1678, 1588, 1280, 1254, 1035, 748.

3,4-Dihydro-2-[4-[4-(3,4-dimethoxycinnamoyl)-piperazino]butyl]-2-(2,5-dimethoxyphenyl)-4-methyl-3-oxo-2H-1,4-benzothiazine oxalate (compound No. 98)

IR: 3033, 2966, 1655, 1585, 1582, 1290, 1275, 1035, 761.

3,4-Dihydro-2-(2,5-dimethoxyphenyl)-2-[4-[4-[2-hydroxy-3-(1-naphthoxy)propyl]piperazino]butyl]-4-methyl-3-oxo-2H-1,4-benzothiazine dioxalate (compound No. 99)

IR: 1662, 1658, 1577, 1288, 1244, 1028, 1023.

EXAMPLE 26

3,4-Dihydro-2-(3,4-dimethoxyphenyl)-4-methyl-2-[3-(N-methyl-3,4,5-trimethoxyphenethylamino)propyl]-3-oxo-2H-1,4-benzothiazine oxalate (compound No. 82)

To a stirred suspension of 60% sodium hydride (0.6 g) in dimethylformamide (5 ml), 3,4-dihydro-2-(3,4-dimethoxyphenyl)-4-methyl-3-oxo-2H-1,4-benzothiazine (4.4 g) dissolved in dimethylformamide (15 ml) is added under nitrogen atmosphere and ice-cooling, and the mixture is stirred for 15 minutes at room temperature. β-Chloropropionaldehyde diethyl acetal (2.8 g) is added to the reaction mixture, and the mixture is stirred for 2.5 hours at 60° C. The mixture is poured into a mixture of ethyl acetate and water. The organic layer is washed with 1N sodium hydroxide and saturated aqueous sodium chloride solution, dried over anhydrous sodium sulfate and concentrated in vacuo. The residue is purified by silica gel column chromatography to give 4.4 g (71.5 %) of 2-(3,3-diethoxypropyl)-3,4-dihydro-2-(3,4-dimethoxyphenyl)-4-methyl-3-oxo-2H-1,4-benzothiazine as an oily form (compound No. 36, (IR: neat, cm$^{-1}$) 1660, 1588, 1444, 1325, 1238, 750).

To a stirred solution of the above product in acetone (15 ml) and water (3 ml), Amberlite CG-120 (Type H, 8.0 g) is added, and the mixture is stirred for 2 hours at 50°-60° C. The reaction mixture is filtered and a mixture of ethyl acetate and water is added to the filtrate. The organic layer is washed with saturated aqueous sodium chloride solution, dried over anhydrous sodium sulfate and concentrated in vacuo to give 2.1 g (57.3%) of 3,4-dihydro-2-(3,4-dimethoxyphenyl)-4-methyl-3-oxo-2-(3-oxopropyl)-2H-1,4-benzothiazine as an oily form (compound No. 37, (IR: neat, cm$^{-1}$) 1726, 1658, 1580, 1243, 1220).

To a stirred solution of the above product in methanol (20 ml), N-methyl-3,4,5-trimethoxyphenethylamine hydrochloride (4.5 g), molecular sieves 3A (2.0 g) and sodium cyanoborohydride (0.4 g) are added, and the mixture is stirred for 1 hour at room temperature. The reaction mixture is filtered.

The filtrate is acidified with 2N hydrochloric acid and concentrated in vacuo. The residual solution is washed with ethyl acetate, alkalized with sodium hydroxide and extracted with ethyl acetate. The organic layer is dried with anhydrous sodium sulfate and concentrated in vacuo. The residual oil is treated by the similar method as in Example 24 to give 0.4 g (11.1%) of the titled compound.

mp. 175.5°-177° C. (ethyl acetate)
IR: 3408, 2576, 1718, 1647, 1586, 1509, 1253, 1235, 1181, 1115, 1016, 752.

Following compound is prepared by the similar method as in Example 26.

3,4-Dihydro-2-(2,5-dimethoxyphenyl)-4-methyl-2-[3-(4-methylpiperazino)propyl]-3-oxo-2H-1,4-benzothiazine dioxalate (compound No. 95)

IR: 3331, 2825, 1663, 1582, 1443, 1255, 1180, 762.

EXAMPLE 27

3,4-Dihydro-2-methoxy-2-[4-[3-(N-methylcyclohexylamino)phenyl]-3-oxo-2H-1,4-benzothiazine hydrochloride (compound No. 100)

To a stirred solution of 2-[4-(3-chloropropoxy)phenyl]-3,4-dihydro-2-methoxy-3-oxo-2H-1,4-benzothiazine (0.3 g, compound No. 38) in acetone (10 ml), sodium iodide (0.2 g) is added, and the mixture is refluxed for 1 hour. The reaction mixture is filtered, and the filtrate is concentrated in vacuo. To a stirred solution of the residual oil in dimethylformamide (2 ml), N-methylcyclohexylamine (0.5 ml) and sodium carbonate (0.2 g) are added, and the mixture is stirred for 1 hour at 80° C. The mixture is poured into a mixture of chloroform and 2N hydrochloric acid and the organic layer is concentrated in vacuo. The residual oil is added to a mixture of ethyl acetate and 1N sodium hydroxide, and the organic layer is dried over anhydrous sodium sulfate and concentrated in vacuo.

The residue is purified by silica gel column chromatography. The product is dissolved in ethyl acetate, and HCl/ethyl acetate is added to the solution. The separated crystals are collected by filtration to give 0.3 g (73.7%) of the titled compound.

mp. 190°-192° C. (dec) (ethyl acetate—methanol).
IR: 3396, 2928, 1677, 1603, 1582, 1508, 1477, 1322, 1244, 1218, 1177, 1074.

Following compounds are prepared by the similar method as in Example 27.

3,4-Dihydro-2-methoxy-2-[5-methoxy-2-[3-(N-methyl-3,4-dimethoxyphenethylamino)propoxy]phenyl]-4-methyl-3-oxo-2H-1,4-benzothiazine hydrochloride (compound No. 129)

IR: 3392, 1654, 1582, 1464, 1260, 1225.

3,4-Dihydro-2-[5-methoxy-2-[3-(N-methyl-3,4-dimethoxyphenethylamino)propoxy]phenyl]-4-methyl-2-methylthio-3-oxo-2H-1,4-benzothiazine hydrochloride (compound No. 131)

IR: 3404, 2924, 1655, 1583, 1509, 1492, 1259, 1234, 1219, 1024.

3,4-Dihydro-2-[5-methoxy-2-[3-[N-methyl-2-(3,4-dimethoxyphenyl)propylamino)propoxy]phenyl]-4-methyl-2-methylthio-3-oxo-2H-1,4-benzothiazine hydrochloride (compound No. 133)

mp. 153°-156.5° (dec) (ethyl acetate).
IR: 3392, 2920, 1654, 1583, 1492, 1465, 1418, 1342, 1256, 1218, 1141, 1023.

3,4-Dihydro-2-[5-methoxy-2-[3-(N-methyl-3,4-dimethoxyphenethylamino)propoxy]phenyl]-4-methyl-2-(4-methylthiobutyl)-3-oxo-2H-1,4-benzothiazine hydrochloride (compound No. 135)

IR: 3396, 2912, 1653, 1583, 1491, 1459, 1341, 1257, 1233, 1216, 1143, 1024.

3,4-Dihydro-2-methoxy-2-[5-methoxy-2-[3-[N-methyl-3-(2,3,4-trimethoxyphenyl)propylamino]propoxy]phenyl]-4-methyl-3-oxo-2H-1,4-benzothiazine hydrochloride (compound No. 140)

IR: 3404, 3388, 2920, 1654, 1583, 1271, 1265, 1217, 1091, 1073, 1069, 1035.

3,4-Dihydro-2-[5-methoxy-2-[3-[N-methyl-3-(2,3,4-trimethoxyphenyl)propylamino]propoxy]phenyl]-4-methyl-2-methylthio-3-oxo-2H-1,4-benzothiazine hydrochloride (compound No. 141)

IR: 2584, 1654, 1598, 1583, 1273, 1258, 1217, 1159, 1142, 1093, 1036, 750.

3,4-Dihydro-2-methoxy-2-[5-methoxy-2-[3-[N-methyl-2-(3,4-methylenedioxyphenoxy)ethylamino]propoxy]phenyl]-4-methyl-3-oxo-2H-1,4-benzothiazine hydrochloride (compound No. 147)

IR: 3400, 2924, 1654, 1479, 1274, 1217, 1183, 1033.

3,4-Dihydro-2-[5-methoxy-2-[3-[N-methyl-2-(3,4-methylenedioxyphenoxy)ethylamino]propoxy]phenyl]-4methyl- 2-methylthio-3-oxo-2H-1,4-benzothiazine hydrochloride (compound No. 149)

mp. 140°-142° C. (ethyl acatate—ethanol).
IR: 2912, 1654, 1582, 1477, 1418, 1274, 1259, 1217, 1183, 1137, 1034, 748.

2-Cyano-3,4-dihydro-4-methyl-3-oxo-2-[4-[3-[4-(p-toluoyl)piperidino]propoxy]phenyl]-2H-1,4-benzothiazine hydrochloride (compound No. 106)

IR: 1655, 1588, 1503, 1479, 1325, 1248, 1220, 1043, 750.

2-(N-Acetylmethylamino)-3,4-dihydro-2-[2-[3-[4-(2-hydroxyethyl)piperazino]propoxy]-5-methoxyphenyl]-4-methyl-3-oxo-2H-1,4-benzothiazine dihydrochloride (compound No. 156)

IR: 1665, 1603, 1583, 1477, 1320, 1266, 1203, 1145, 1025.

EXAMPLE 28

3,4-Dihydro-4-methyl-2-[4-[4-(N-methyl-3,4-dimethoxyphenethylamino)butoxy]phenyl]-2-methylthiol-3-oxo-2H-1,4l-benzothiazine hydrochloride (compound No. 103)

To a stirred solution of 2-[4-(4-bromobutoxy)phenyl]-3,4-dihydro-4l-methyl-2-methylthio-3-oxo-2H-1,4-benzothiazine (1.0 g, compound No. 42) and N-methyl-homoveratrylamine (0.7 g) in dimethylformamide (5 ml), sodium carbonate (0.4 g) is added, and the mixture is stirred for 1 hour at 70° C. The reaction mixture is poured into a mixture of chloroform and 2N hydrochloric acid, and the organic layer is concentrated in vacuo. The residual oil is added to a mixture of ethyl acetate and 2N sodium hydroxide. The organic layer is washed with saturated aqueous sodium chloride solution, dried over anhydrous sodium sulfate and concentrated in vacuo. The residue is purified by silica gel column chromatography. The product is dissolved in ethyl acetate, and HCl/ethyl acetate is added to the solution. The separated crystals are collected by filtration to give 1.0 g (74.3%) of the titled compound.

mp. 146°–147.5° C. (ethyl acetate—methanol).
IR: 3400, 2916, 2584, 1654, 1602, 1583, 1506, 1464, 1341, 1253, 1140, 1023.

Following compound is prepared by the similar method as in Example 28.

3,4-Dihydro-2-methoxy-2-[5-methoxy-2-[4-(N-methyl-3,4-dimethoxyphenethylamino)butoxy]phenyl]-4-methyl-3-oxo-2H-1,4-benzothiazine hydrochloride (compound No. 130)

IR: 3400, 2924, 1662, 1584, 1492, 1419, 1350, 1261, 1222, 1143, 1026, 753. 3,4-Dihydro-2-[5-methoxy-2-[4-(N-methyl-3,4-dimethoxyphenethylamino)butoxy]-phenyl]-4-methyl-2-methylthio-3-oxo-2H-1,4-benzothiazine hydrochloride (compound No. 132)

IR: 3416, 2920, 1654, 1583, 1509, 1490, 1465, 1259, 1219, 1141, 1024, 751.

3,4-Dihydro-2-[5-methoxy-2-[4-[N-methyl-2-(3,4-dimethoxyphenyl)propylamino]butoxy]phenyl]-4-methyl-2-methylthio-3-oxo-2H-1,4-benzothiazine hydrochloride (compound No. 134)

IR: 3400, 2920, 1655, 1582, 1464, 1419, 1342, 1256, 1219, 1141, 1022, 751.

2-(N-Acetylmethylamino)-3,4-dihydro-2-[5-methoxy-2-[4-(N-methyl-3,4-dimethoxyphenethylamino)butoxy]phenyl]-4-methyl-3-oxo-2H-1,4-benzothiazine hydrochloride (compound No. 137)

mp. 122°–124° C. (ethyl acatate—methanol).
IR: 3400, 2920, 1663, 1655, 1584, 1498, 1466, 1255, 1228, 1151, 1137, 1022.

3,4-Dihydro-2-[5-methoxy-2-[4-(N-methyl-3,4,5-trimethoxyphenethylamino)butoxy]phenyl]-4-methyl-2-methylthio-3-oxo-2H-1,4-benzothiazine hydrochloride (compound No. 142)

mp. 193°–195° C. (ethyl acatate—methanol).
IR: 3400, 2920, 2832, 1654, 1584, 1275, 1245, 1233, 1219, 1120, 1038, 1004.

3,4-Dihydro-2-methoxy-2-[5-methoxy-2-[4-[N-methyl-2-(3,4-methylenedioxyphenoxy)ethylamino]butoxy]-phenyl]-4-methyl-3-oxo-2H-1,4-benzothiazine hydrochloride (compound No. 148)

IR: 3400, 2924, 1660, 1583, 1478, 1273, 1220, 1183, 1132, 1094, 1033, 751.

3,4-Dihydro-2-[5-methoxy-2-[4-[N-methyl-2-(3,4-methylenedioxyphenoxy)ethylamino]butoxy]phenyl]-4-methyl-2-methylthio-3-oxo-2H-1,4-benzothiazine hydrochloride hemihydrate (compound No. 150)

mp. 156°–158° C. (ethyl acetate—ethanol).
IR: 3404, 2912, 1654, 1478, 1274, 1259, 1217, 1183, 1033.

3,4-Dihydro-2-[4-(4-dimethylaminobutoxy)phenyl]-2-(3-dimethylaminopropyl)-4-methyl-3-oxo-2H-1,4-benzothiazine dioxalate (compound No. 158)

mp. 115°–117° C. (dec.) (methanol—ethanol).
IR: 3408, 2660, 1716, 1699, 1634, 1605, 1583, 1503, 1231, 1221, 1177, 718.

3,4-Dihydro-2-(3-dimethylaminopropyl)-4-methyl-2-[4-[4-(N-methylcyclohexylamino)butoxy]phenyl]-3-oxo-2H-1,4-benzothiazine dihydrochloride (compound No. 160)

IR: 3392, 2660, 1647, 1466, 1350, 1244, 1176, 755.

3,4-Dihydro-2-(3-dimethylaminopropyl)-2-[4-[4-(N-methyl-3,4-dimethoxyphenethylamino)butoxy]phenyl]-4-methyl-3-oxo-2H-1,4-benzothiazine dioxalate (compound No. 161)

mp. 122°–125° C. (ethyl acetate—methanol).
IR: 3404, 2644, 1716, 1700, 1636, 1508, 1464, 1399, 1350, 1235, 1177, 718.

3,4-Dihydro-2-(3-dimethylaminopropyl)-4-methyl-2-[4-[4-[N-methyl-3-(2,3,4-trimethoxyphenyl)propylamino]butoxy]phenyl]-3-oxo-2H-1,4-benzothiazine dihydrochloride (compound No. 162)

IR: 3372, 2652, 1647, 1490, 1460, 1249, 1093, 1010, 750.

2-[4-[4-(4-Benzoylpiperidino)butoxy]phenyl]-3,4-dihydro-4-methyl-2-methylthio-3-oxo-2H-1,4-benzothiazine hydrochloride (compound No. 105)

IR: 1664, 1601, 1500, 1472, 1223, 1028, 750.

2-[2-[4-[4-(p-Anisoyl)piperidino]butoxy]-5-methoxyphenyl]-3,4-dihydro-2-methoxy-4-methyl-3-oxo-2H-1,4-benzothiazine hydrochloride (compound No. 155)

IR: 1664, 1485, 1201, 1045, 744.

3,4-Dihydro-2-[5-methoxy-2-4-(N-methyl-3,4-dimethoxyphenethylamino)butoxy]phenyl]-2,4-dimethyl-3-oxo-2H-1,4-benzothiazine oxalate (compound No. 127)

mp. 184°–185° C. (dec.) (chloroform—methanol).

IR: 3396, 2912, 1653, 1583, 1465, 1410, 1342, 1276, 1256, 1221, 1154, 1140.

3,4-Dihydro-2,4-dimethyl-2-[4-[4-(N-methyl-3,4-dimethoxyphenethylamino)butoxy]phenyl]-3-oxo-2H-1,4-benzothiazine oxalate (compound No. 108)

mp. 146°-148° C. (dec.) (isopropanol).
IR: 3388, 2920, 1650, 1509, 1457, 1369, 1237, 1179, 1154, 1022, 751.

3,4-Dihydro-4,7-dimethyl-2-[5-methoxy-2-[4-(N-methyl-3,4-dimethoxyphenethylamino)butoxy]phenyl]-3-oxo-2H-1,4-benzothiazine oxalate (compound No. 138)

mp. 148°-150° C. (ethanol).
IR: 1672, 1498, 1464, 1255, 1239, 1218, 1132, 1031, 806, 475.

3,4-Dihydro-4,7-dimethyl-2-[4-[4-(N-methyl-3,4-dimethoxyphenethylamino)butoxy]phenyl]-3-oxo-2H-1,4-benzothiazine oxalate (compound No. 111)

mp. 99°-102° C.
IR: 2912, 1647, 1603, 1507, 1493, 1451, 1396, 1233, 1173, 1134, 1021, 492.

7-Chloro-3,4-dihydro-2-[5-methoxy-2-[4-(N-methyl-3,4-dimethoxyphenethylamino)butoxy]phenyl]-4-methyl-3-oxo-2H-1,4-benzothiazine fumarate (compound No. 139)

mp. 71°-75° C.
IR: 3380, 1653, 1498, 1464, 1259, 1235.

7-Chloro-3,4-dihydro-4-methyl-2-[4-[4-(N-methyl-3,4-dimethoxyphenethylamino)butoxy]phenyl]-3-oxo-2H-1,4-benzothiazine fumarate (compound No. 114)

mp. 117°-120° C. (ethanol—isopropylether).
IR: 3400, 1667, 1464, 1252, 1238.

2-(N-Acetylmethylamino)-3,4-dihydro-2-[5-methoxy-2-[4-[N-methyl-2-(3,4-methylenedioxyphenoxy)ethylamino]butoxy]phenyl]-4-methyl-3-oxo-2H-1,4-benzothiazine hydrochloride (compound No. 152)

mp. 181°-183° C. (ethyl acetate—methanol).
IR: 3376, 2904, 1662, 1583, 1277, 1222, 1185, 1134, 1107, 1030, 837.

3,4-Dihydro-2,4-dimethyl-2-[5-methoxy-2-[5-(N-methylcyclohexylamino)pentyloxy]phenyl]-3-oxo-2H-1,4-benzothiazine fumarate (compound No. 122)

mp. 85°-87.5° C. (dec.) (isopropanol—n-hexane).
IR: 3396, 2920, 2860, 1660, 1583, 1466, 1341, 1274, 1255, 1215, 1159, 1037, 980, 749.

3,4-Dihydro-2,4-dimethyl-2-[4-[5-(N-methylcyclohexylamino)pentyloxy]phenyl]-3-oxo-2H-1,4-benzothiazine oxalate (compound No. 109)

mp. 149°-151° C. (isopropanol—n-hexane).
IR: 3404, 2924, 2856, 1652, 1506, 1367, 1400, 1348, 1277, 1243, 1179, 1110, 747, 719.

3,4-Dihydro-4,7-dimethyl-2-[5-methoxy-2-[5-(N-methylcyclohexylamino)pentyloxy]phenyl]-3-oxo-2H-1,4-benzothiazine oxalate (compound No. 124)

mp. 85°-87° C. (isopropanol—n-hexane).
IR: 2920, 1663, 1493, 1465. 1352, 1269, 1236, 1206, 1039.

3,4-Dihydro-4,7-dimethyl-2-[4-[5-(N-methylcyclohexylamino)pentyloxy]phenyl]-3-oxo-2H-1,4-benzothiazine oxalate (compound No. 112)

mp. 90°-105° C.
IR: 2916, 1653, 1608, 1508, 1396, 1351, 1239.

7-Chloro-3,4-dihydro-2-[5-methoxy-2-[5-(N-methylcyclohexylamino)pentyloxy]phenyl]-4-methyl-3-oxo-2H-1,4-benzothiazine fumarate (compound No. 126)

mp. 139°-143° C. (ethanol).
IR: 2916, 1647, 1473, 1241, 1215.

7-Chloro-3,4-dihydro-4-methyl-2-[4-[5-(N-methylcyclohexylamino)pentyloxy]phenyl]-3-oxo-2H-1,4-benzothiazine oxalate (compound No. 115)

mp. 120°-123° C. (ethanol—isopropylether).
IR: 3400, 1660, 1607, 1474, 1238, 1174.

3,4-Dihydro-2,4-dimethyl-2-[5-methoxy-2-[3-[N-methyl-2-(3,4-methylenedioxyphenoxy)ethylamino]propoxy]phenyl]-3-oxo-2H-1,4-benzothiazine fumarate (compound No. 143)

mp. 133°-134° C. (ethyl acetate).
IR: 3392, 1654, 1478, 1271, 1260, 1212, 1034, 748.

3,4-Dihydro-2,4-dimethyl-2-[5-methoxy-2-[4-[N-methyl-2-(3,4-methylenedioxyphenoxy)ethylamino]butoxy]phenyl]-3-oxo-2H-1,4-benzothiazine fumarate (compound No. 144)

mp. 120°-121° C. (ethyl acetate).
IR: 3388, 2920, 1664, 1478, 1272, 1213, 1183, 1034.

EXAMPLE 29

3,4-Dihydro-2-(3-dimethylaminopropyl)-4-methyl-2-[4-[3-(N-methylcyclohexylamino)propoxy]phenyl]-3-oxo-2H-1,4-benzothiazine dioxalate hemihydrate (compound No. 159)

To a stirred suspension of 60% sodium hydride (0.2 g) in dimethylformamide (3 ml), 3,4-dihydro-2-(3-dimethylaminopropyl)-2-(4-hydroxyphenyl)-4-methyl-3-oxo-2H-1,4-benzothiazine (1.4 g, compound No. 75) dissolved in dimethylformamide (5 ml) is added under nitrogen atmosphere, and the mixture is stirred for 15 minutes at room temperature. A solution of N-(3-methanesulfonyloxypropyl)-N-methylcyclohexylamine in dimethylformamide [prepared by mixing of N-(3-methanesulfonyloxypropyl)-N-methylcyclohexylamine hydrochloride (13.8 g) and triethylamine (0.7 ml) in dimethylformamide (6 ml), and followed by filtraton to remove precipitate] is added to the reaction mixture, and the mixture stirred for 1 hour at 55° C. The mixture is poured into a mixture of ethyl acetate and 1N hydrochloric acid. The aqueous layer is washed with chloroform, alkalized with 2N sodium hydroxide, and extracted with ethyl acetate. The organic layer is washed with saturated aqueous sodium chloride solution, dried over anhydrous sodium sulfate and concentrated in vacuo. To the residual oil, oxalic acid in ethanol is added and the separated crystals are collected by filtration to give 1.7 g (60.7%) of the titled compound.

mp 165°-167° C. (dec.) (ethanol—water).
IR: 3420, 2640, 1716, 1700, 1644, 1607, 1584, 1505, 1240, 1216, 1177, 719.

Following compound is prepared by the similar method as in Example 29.

3,4-Dihydro-2-methoxy-4-methyl-2-[4-[3-[(N-methylcyclohexylamino)propoxy]phenyl]-3-oxo-2H-1,4-benzothiazine hydrochloride (compound No. 101)

IR: 3338, 2920, 2856, 2584, 1660, 1604, 1508, 1462, 1456, 1350, 1245, 1225.

2-Cyano-3,4-dihydro-4-methyl-2-[4-[3-(N-methylcyclohexylamino)propoxy]phenyl]-3-oxo-2H-1,4-benzothiazine hydrochloride (compound No. 102)

IR: 3404, 2924, 2608, 2214, 1664, 1604, 1583, 1508, 1467, 1251, 1181, 753.

2-(N-Acetylmethylamino)-3,4-dihydro-4-methyl-2-[4-[3-(N-methylcyclohexylamino)propoxy]phenyl]-3-oxo-2H-1,4-benzothiazine (compound No. 104)

mp. 119°–120° C. (isopropylether—methanol).
IR: 2916, 2848, 1656, 1606, 1581, 1509, 1466, 1301, 1284, 1249, 1179, 1145.

2-[4-[3-(4-Benzylpiperidino)propoxy]phenyl]-3,4-dihydro-2-(3-dimethylaminopropyl)-4-methyl-3-oxo-2H-1,4-benzothiazine dioxalate (compound No. 163)

IR: 3024, 3016, 2725, 1655, 1519, 1423, 1244, 1025.

2-[4-[3-[4-(4-Chlorobenzoyl)piperidino]propoxy]phenyl]-3,4-dihydro-2-(3-dimethylaminopropyl)-4-methyl-3-oxo-2H-1,4-benzothiazine dioxalate (compound No. 164)

IR: 1658, 1588, 1441, 1305, 1278, 1262, 1220, 1048, 1024, 733.

3,4-Dihydro-2,4-dimethyl-2-[2-(3-dimethylaminopropoxy)-5-methoxyphenyl]-3-oxo-2H-1,4-benzothiazine fumarate (compound No. 121)

mp. 154°–155.5° C. (isopropanol—n-hexane).
IR: 3404, 2928, 1654, 1584, 1472, 1342, 1275, 1258, 1215, 1038, 980.

3,4-Dihydro-4,7-dimethyl-2-[2-(3-dimethylaminopropoxy)-5-methoxyphenyl]-3-oxo-2H-1,4-benzothiazine fumarate (compound No. 123)

mp. 163°–164° C. (ethanol).
IR: 1664, 1493, 1352, 1279, 1245, 1219, 1049.

3,4-Dihydro-4,7-dimethyl-2-[4-(3-dimethylaminopropoxy)phenyl]-3-oxo-2H-1,4-benzothiazine fumarate (compound No. 110)

mp. 120°–122° C. (ethanol).
IR: 1651, 1604, 1493, 1467, 1350, 1297, 1238, 1172, 978, 802.

7-Chloro-3,4-dihydro-[2-(3-dimethylaminopropoxy)-5-methoxyphenyl]-4-methyl-3-oxo-2H-1,4-benzothiazine fumarate (compound No. 125)

mp. 184°–186° C. (ethanol).

IR: 3380, 1654, 1470, 1238, 1211.

7-Chloro-3,4-dihydro-2-[4-(3-dimethylaminopropoxy)phenyl]-4-methyl-3-oxo-2H-1,4-benzothiazine fumarate (compound No. 113)

mp. 161°–163° C. (ethanol).
IR: 3400, 1659, 1473, 1238, 644.

EXAMPLE 30

3,4-Dihydro-2-[4-(3-dimethylaminopropoxy)phenyl]-2-(3-dimethylaminopropyl)-4-methyl-3-oxo-2H-1,4-benzothiazine dioxalate ½ ethanol (compound No. 157)

To a stirred suspension of 60% sodium hydride (1.0 g) in dimethylformamide (5 ml), 3,4-dihydro-2-(4-hydroxyphenyl)-4-methyl-3-oxo-2H-1,4-benzothiazine (3.0 g) and 3-dimethylaminopropyl chloride hydrochloride (2.1 g) in dimethylformamide (12 ml) is added under nitogen atmosphere, and the mixture is stirred for 3.5 hours at 85°–90° C. The reaction mixture is poured into a mixture of benzene and water. The organic layer is washed with 1N potassium hydroxide and then saturated aqueous sodium chloride solution, dried over anhydrous sodium sulfate and concentrated in vacuo. The residue is purified by silica gel column chromatography. The product is dissolved in ethyl acetate, and oxalic acid in ethyl acetate is added to the solution and the separated crystals are collected by filtration to give 2.0 g (28.1%) of the titled compound.

mp. 140.5°–143° C. (dec.) (ethanol—water).
IR: 3420, 2676, 1718, 1701, 1638, 1607, 1584, 1509, 1277, 1228, 1179, 718.

EXAMPLE 31

3,4-Dihydro-2-[5-methoxy-2-[3-[N-methyl-2-(3,4-dimethoxyphenyl)propylamino]propoxy]phenyl]-4-methyl-2-methylthio-3-oxo-2H-1,4-benzothiazine hydrochloride (compound No. 133)

3,4-Dihydro-2-(2-hydroxy-5-methoxyphenyl)-4-methyl-2-methylthio-3-oxo-2H-1,4-benzothiazine (5.2 g, compound No. 8), β-chloropropionaldehyde diethyl acetate (3.0 g) and N-methyl-2-(3,4-dimethoxyphenyl)-propylamine hydrochloride (5.2 g) are treated by the similar method as in Example 26 to give 4.7 g (64.9%) of 2-[2-(3,3-diethoxypropoxy)-5-methoxyphenyl]-3,4-dihydro-4-methyl-2-methylthio-3-oxo-2H-1,4-benzothiazine (compound No. 21, (IR: neat, cm$^{-1}$) 1660, 1555, 1048, 750), 2.8 g (72.0%) of 3,4-dihydro-2-[5-methoxy-2-(3-oxopropoxy)phenyl]-4-methyl-2-methylthio-3-oxo-2H-1,4-benzothiazine (compound No. 22, (IR: neat, cm$^{-1}$) 1722, 1658, 1588, 1036, 748) and 0.6 g (12.8%) of the titled compound (mp. 153°–156.5° C. (dec.)).

TABLE 1

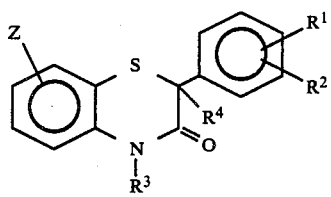

| compound No. | R¹ | R² | R³ | R⁴ | Z |
|---|---|---|---|---|---|
| 1 | 4-OH | —H | —H | —Cl | —H |
| 2 | 4-OH | —H | —CH₃ | —Cl | —H |
| 3 | 2-OH | 5-OCH₃ | —CH₃ | —Cl | —H |
| 4 | 4-OH | —H | —H | —OCH₃ | —H |
| 5 | 4-OH | —H | —CH₃ | —OCH₃ | —H |
| 6 | 2-OH | 5-OCH₃ | —CH₃ | —OCH₃ | —H |
| 7 | 4-OH | —H | —CH₃ | —SCH₃ | —H |
| 8 | 2-OH | 5-OCH₃ | —CH₃ | —SCH₃ | —H |
| 9 | 4-OH | | —CH₃ | —S—C₆H₅ | —H |
| 10 | 4-OH | —H | —CH₃ | —CN | —H |
| 11 | 4-OH | —H | —CH₃ | —OH | —H |
| 12 | 2-OH | 5-OCH₃ | —CH₃ | —CH₃ | —H |
| 13 | 4-OH | —H | —CH₃ | —CH₃ | —H |
| 14 | 2-OH | 5-OCH₃ | —CH₃ | —H | 7-CH₃ |
| 15 | 4-OH | —H | —CH₃ | —H | 7-CH₃ |
| 16 | 2-OH | 5-OCH₃ | —CH₃ | —H | 7-Cl |
| 17 | 4-OH | —H | —CH₃ | —H | 7-Cl |
| 18 | 2-OH | 5-OCH₃ | —CH₃ | —CH(CH₃)₂ | —H |
| 19 | 4-OH | —H | —CH₃ | —CH(CH₃)₂ | —H |
| 20 | 4-OCOCH₃ | —H | —CH₃ | —OCH₃ | —H |
| 21 | 2-OCH₂CH₂CH(OC₂H₅)₂ | 5-OCH₃ | —CH₃ | —SCH₃ | —H |
| 22 | 2-OCH₂CH₂CHO | 5-OCH₃ | —CH₃ | —SCH₃ | —H |
| 23 | 4-OCH₂—CH—CH₂ (epoxide) | —H | —CH₃ | —CN | —H |
| 24 | 4-OCH₂CH(OH)CH₂NHC(CH₃)₃ | —H | —CH₃ | —CN | —H |
| 25* | 2-OCH₂CH(OH)CH₂N(piperazine)NCH₂C₆H₅ | 5-OCH₃ | —CH₃ | —OCH₃ | —H |
| 26 | 2-OCH₂CH(OH)CH₂NHC(CH₃)₃ | 5-OCH₃ | —CH₃ | —N(CH₃)COCH₃ | —H |

*: hydrochloride

TABLE 2

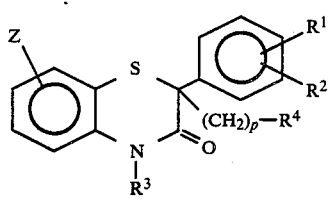

| compound No. | R¹ | R² | R³ | R⁴ | Z | p |
|---|---|---|---|---|---|---|
| 27 | 2-OCH₃ | 5-OCH₃ | —CH₃ | —Cl | —H | 3 |
| 28 | 3-OCH₃ | 4-OCH₃ | —CH₃ | —Cl | —H | 3 |
| 29 | 4-OCH₃ | —H | —CH₃ | —Br | —H | 3 |
| 30 | 4-OCH₃ | —H | —CH₃ | —Br | —H | 4 |
| 31 | 2-OCH₃ | 5-OCH₃ | —CH₃ | —Br | —H | 4 |
| 32 | 3-OCH₃ | 4-OCH₃ | —CH₃ | —Br | —H | 4 |
| 33 | 2-OCH₃ | 5-OCH₃ | —CH₃ | —Br | —H | 5 |

TABLE 2-continued

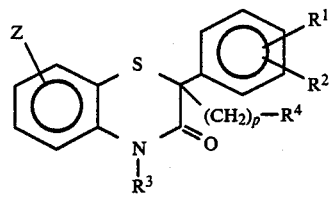

| compound No. | R¹ | R² | R³ | R⁴ | Z | p |
|---|---|---|---|---|---|---|
| 34 | 2-O-(tetrahydropyran-2-yl) | 5-OCH₃ | —CH₃ | —Br | —H | 4 |
| 35 | 2-OH | 5-OCH₃ | —CH₃ | —SCH₃ | —H | 4 |
| 36 | 3-OCH₃ | 4-OCH₃ | —CH₃ | —CH(OC₂H₅)₂ | —H | 2 |
| 37 | 3-OCH₃ | 4-OCH₃ | —CH₃ | —CHO | —H | 2 |
| 38 | 4-O—(CH₂)₃—Cl | —H | —H | —OCH₃ | —H | 0 |
| 39 | 2-O—(CH₂)₃—Cl | 5-OCH₃ | —CH₃ | —OCH₃ | —H | 0 |
| 40 | 2-O—(CH₂)₄—Br | 5-OCH₃ | —CH₃ | —OCH₃ | —H | 0 |
| 41 | 2-O—(CH₂)₃—Cl | 5-OCH₃ | —CH₃ | —SCH₃ | —H | 0 |
| 42 | 4-O—(CH₂)₄—Br | —H | —CH₃ | —SCH₃ | —H | 0 |
| 43 | 2-O—(CH₂)₄—Br | 5-OCH₃ | —CH₃ | —SCH₃ | —H | 0 |
| 44 | 2-O—(CH₂)₃—Cl | 5-OCH₃ | —CH₃ | —SCH₃ | —H | 4 |
| 45 | 2-O—(CH₂)₃—Br | 5-OCH₃ | —CH₃ | —H | —H | 1 |
| 46 | 2-O—(CH₂)₄—Br | 5-OCH₃ | —CH₃ | —H | —H | 1 |
| 47 | 2-O—(CH₂)₅—Br | 5-OCH₃ | —CH₃ | —H | —H | 1 |
| 48 | 4-O—(CH₂)₃—Br | —H | —CH₃ | —H | —H | 1 |
| 49 | 4-O—(CH₂)₄—Br | —H | —CH₃ | —H | —H | 1 |
| 50 | 4-O—(CH₂)₅—Br | —H | —CH₃ | —H | —H | 1 |
| 51 | 2-O—(CH₂)₃—Br | 5-OCH₃ | —CH₃ | —H | 7-CH₃ | 0 |
| 52 | 2-O—(CH₂)₄—Br | 5-OCH₃ | —CH₃ | —H | 7-CH₃ | 0 |
| 53 | 2-O—(CH₂)₅—Br | 5-OCH₃ | —CH₃ | —H | 7-CH₃ | 0 |
| 54 | 4-O—(CH₂)₃—Br | —H | —CH₃ | —H | 7-CH₃ | 0 |
| 55 | 4-O—(CH₂)₄—Br | —H | —CH₃ | —H | 7-CH₃ | 0 |
| 56 | 4-O—(CH₂)₅—Br | —H | —CH₃ | —H | 7-CH₃ | 0 |
| 57 | 2-O—(CH₂)₃—Br | 5-OCH₃ | —CH₃ | —H | 7-Cl | 0 |
| 58 | 2-O—(CH₂)₄—Br | 5-OCH₃ | —CH₃ | —H | 7-Cl | 0 |
| 59 | 2-O—(CH₂)₅—Br | 5-OCH₃ | —CH₃ | —H | 7-Cl | 0 |
| 60 | 4-O—(CH₂)₃—Br | —H | —CH₃ | —H | 7-Cl | 0 |
| 61 | 4-O—(CH₂)₄—Br | —H | —CH₃ | —H | 7-Cl | 0 |
| 62 | 4-O—(CH₂)₅—Br | —H | —CH₃ | —H | 7-Cl | 0 |
| 63 | 2-O—(CH₂)₃—Br | 5-OCH₃ | —CH₃ | —CH(CH₃)₂ | —H | 0 |
| 64 | 2-O—(CH₂)₄—Br | 5-OCH₃ | —CH₃ | —CH(CH₃)₂ | —H | 0 |
| 65 | 4-O—(CH₂)₃—Br | —H | —CH₃ | —CH(CH₃)₂ | —H | 0 |

TABLE 3

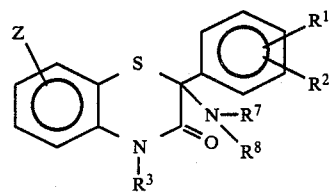

| compound No. | R¹ | R² | R³ | R⁷ | R⁸ | Z |
|---|---|---|---|---|---|---|
| 66 | 4-OH | —H | —CH₃ | —H | —CH₃ | —H |
| 67 | 2-OH | 5-OCH₃ | —CH₃ | —H | —CH₃ | —H |
| 68 | 4-OCOCH₃ | —H | —CH₃ | —H | —CH₃ | —H |
| 69 | 4-OH | —H | —CH₃ | —CH₃ | —COCH₃ | —H |
| 70 | 4-OCOCH₃ | —H | —CH₃ | —CH₃ | —COCH₃ | —H |
| 71 | 2-OH | 5-OCH₃ | —CH₃ | —CH₃ | —COCH₃ | —H |
| 72 | 2-OCOCH₃ | 5-OCH₃ | —CH₃ | —CH₃ | —COCH₃ | —H |
| 73 | 2-O—(CH₂)₄—Br | 5-OCH₃ | —CH₃ | —CH₃ | —COCH₃ | —H |
| 74 | 2-OCH₂CH(O)CH₂ (epoxide) | 5-OCH₃ | —CH₃ | —CH₃ | —COCH₃ | —H |

TABLE 4

[Structure: benzothiazepinone-like compound with substituents Z, R¹, R², R³, R⁷, R⁸, and (CH₂)p linker]

| compound No. | R¹ | R² | R³ | R⁷ | R⁸ | Z | p |
|---|---|---|---|---|---|---|---|
| 75 | 4-OH | —H | —CH₃ | —CH₃ | —CH₃ | —H | 3 |
| 76 | 4-O-(tetrahydropyran-2-yl) | | —H | —CH₃ | —CH₃ | —CH₃ | —H | 3 |
| 77*¹ | 4-OCH₃ | —H | —CH₃ | —CH₃ | —CH₃ | —H | 3 |
| 78*¹ | 2-OCH₃ | 5-OCH₃ | —CH₃ | —CH₃ | —CH₃ | —H | 3 |
| 79*¹ | 3-OCH₃ | 4-OCH₃ | —CH₃ | —CH₃ | —CH₃ | —H | 3 |
| 80*¹ | 2-OCH₃ | 5-OCH₃ | —CH₃ | —CH₃ | cyclohexyl (H) | —H | 3 |
| 81*¹ | 2-OCH₃ | 5-OCH₃ | —CH₃ | —CH₃ | —(CH₂)₂—(3,4-dimethoxyphenyl) | —H | 3 |
| 82*¹ | 3-OCH₃ | 4-OCH₃ | —CH₃ | —CH₃ | —(CH₂)₂—(3,4,5-trimethoxyphenyl) | —H | 3 |
| 83*¹ | 2-OCH₃ | 5-OCH₃ | —CH₃ | —CH₃ | —(CH₂)₂—(3,4,5-trimethoxyphenyl) | —H | 3 |
| 84*¹ | 3-OCH₃ | 4-OCH₃ | —CH₃ | —CH₃ | —(CH₂)₂O—(3,4-methylenedioxyphenyl) | —H | 3 |
| 85*¹ | 2-OCH₃ | 5-OCH₃ | —CH₃ | —CH₃ | —(CH₂)₂O—(3,4-methylenedioxyphenyl) | —H | 3 |
| 86*² | 2-OCH₃ | 5-OCH₃ | —CH₃ | —CH₃ | —(CH₂)₂O—(3,4,5-trimethoxyphenyl) | —H | 3 |

TABLE 4-continued

| compound No. | R¹ | R² | R³ | R⁷ | R⁸ | Z | p |
|---|---|---|---|---|---|---|---|
| 87*² | 2-OCH₃ | 5-OCH₃ | —CH₃ | —CH₃ | —(CH₂)₂O—(2,3-dimethoxyphenyl) | —H | 3 |
| 88*¹ | 3-OCH₃ | 4-OCH₃ | —CH₃ | —CH₃ | —(CH₂)₂—(3,4,5-trimethoxyphenyl) | —H | 4 |
| 89*¹ | 2-OCH₃ | 5-OCH₃ | —CH₃ | —CH₃ | —(CH₂)₂O—(3,4-methylenedioxyphenyl) | —H | 4 |
| 90*² | 2-OCH₃ | 5-OCH₃ | —CH₃ | —CH₃ | —(CH₂)₂O—(3,4-methylenedioxyphenyl) | —H | 5 |
| 91*¹ | 4-OCH₃ | —H | —CH₃ | —CH₃ | —(CH₂)₂O—(3,4-methylenedioxyphenyl) | —H | 3 |
| 92*² | 4-O—(CH₂)₄—Br | —H | —CH₃ | —CH₃ | —CH₃ | —H | 3 |
| 93*¹ | 3-OCH₃ | 4-OCH₃ | —CH₃ | | cyclohexyl-CH(CO-4-fluorophenyl)— | —H | 3 |
| 94*² | 3-OCH₃ | 4-OCH₃ | —CH₃ | | cyclohexyl-CH(OH)-phenyl | —H | 4 |
| 95*³ | 2-OCH₃ | 5-OCH₃ | —CH₃ | | N-methylpiperidin-4-yl (R⁷, R⁸ forming ring) | —H | 3 |
| 96*³ | 2-OCH₃ | 5-OCH₃ | —CH₃ | | piperidine-N—(CH₂)₂—(3,4-dimethoxyphenyl) | —H | 3 |

TABLE 4-continued

Structure: benzothiazepinone core with substituents Z, R¹, R², R³, R⁷, R⁸, (CH₂)ₚ

| compound No. | R¹ | R² | R³ | R⁷ | R⁸ | Z | p |
|---|---|---|---|---|---|---|---|
| 97*³ | 3-OCH₃ | 4-OCH₃ | —CH₃ | piperidinyl | —(CH₂)₂—(3,4,5-trimethoxyphenyl) | —H | 3 |
| 98*¹ | 2-OCH₃ | 5-OCH₃ | —CH₃ | piperidinyl | —COCH=CH—(3,4-dimethoxyphenyl) | —H | 4 |
| 99*³ | 2-OCH₃ | 5-OCH₃ | —CH₃ | piperidinyl | —CH₂CH(OH)CH₂—O—(1-naphthyl) | —H | 4 |

*¹oxalate
*²hydrochloride
*³dioxalate

TABLE 5

Structure: benzothiazepinone core with O—(CH₂)ₘ—NR⁵R⁶ substituent

| compound No. | R³ | R⁴ | R⁵ | R⁶ | Z | m |
|---|---|---|---|---|---|---|
| 100*¹ | —H | —OCH₃ | —CH₃ | cyclohexyl | —H | 3 |
| 101*¹ | —CH₃ | —OCH₃ | —CH₃ | cyclohexyl | —H | 3 |
| 102*¹ | —CH₃ | —CN | —CH₃ | cyclohexyl | —H | 3 |
| 103*¹ | —CH₃ | —SCH₃ | —CH₃ | —(CH₂)₂—(3,4-dimethoxyphenyl) | —H | 4 |

TABLE 5-continued

Structure: Z-substituted benzothiazine with R³ on N, R⁴ on C adjacent to C=O, linked to phenyl-O-(CH₂)ₘ-N(R⁵)(R⁶)

| compound No. | R³ | R⁴ | R⁵ | R⁶ | Z | m |
|---|---|---|---|---|---|---|
| 104 | —CH₃ | —N(CH₃)COCH₃ | —CH₃ | cyclohexyl | —H | 3 |
| 105*¹ | —CH₃ | —SCH₃ | | cyclohexyl-CO-phenyl | —H | 4 |
| 106*¹ | —CH₃ | —CN | | cyclohexyl-CO-(4-CH₃-phenyl) | —H | 3 |
| 107*³ | —CH₃ | —CH₃ | —CH₃ | —CH₃ | —H | 3 |
| 108*² | —CH₃ | —CH₃ | —CH₃ | —(CH₂)₂—(3,4-dimethoxyphenyl) | —H | 4 |
| 109*² | —CH₃ | —CH₃ | —CH₃ | cyclohexyl | —H | 5 |
| 110*³ | —CH₃ | —H | —CH₃ | —CH₃ | 7-CH₃ | 3 |
| 111*² | —CH₃ | —H | —CH₃ | —(CH₂)₂—(3,4-dimethoxyphenyl) | 7-CH₃ | 4 |
| 112*² | —CH₃ | —H | —CH₃ | cyclohexyl | 7-CH₃ | 5 |
| 113*³ | —CH₃ | —H | —CH₃ | —CH₃ | 7-Cl | 3 |
| 114*³ | —CH₃ | —H | —CH₃ | —(CH₂)₂—(3,4-dimethoxyphenyl) | 7-Cl | 4 |
| 115*² | —CH₃ | —H | —CH₃ | cyclohexyl | 7-Cl | 5 |

TABLE 5-continued

Structure: Z-substituted benzothiazine with R³ on N, R⁴ on C, carbonyl, phenyl-O-(CH₂)ₘ-N(R⁵)(R⁶)

| compound No. | R³ | R⁴ | R⁵ | R⁶ | Z | m |
|---|---|---|---|---|---|---|
| 116*² | —CH₃ | —CH₃ | —CH₃ | —(CH₂)₂O—(3,4,5-trimethoxyphenyl) | —H | 3 |
| 117*² | —CH₃ | —CH₃ | —CH₃ | —(CH₂)₂—(3,4-methylenedioxyphenyl) | —H | 4 |
| 118*² | —CH₃ | —CH(CH₃)₂ | —CH₃ | —(CH₂)₂O—(3,4-dimethoxyphenyl) | —H | 3 |
| 119*² | —CH₃ | —CH(CH₃)₂ | —CH₃ | —(CH₂)₂—(3,4-dimethoxyphenyl) | —H | 4 |
| 120*² | —CH₃ | —CH(CH₃)₂ | —CH₃ | —(CH₂)₂—(3,4-dimethoxyphenyl) | —H | 5 |

*¹hydrochloride
*²oxalate
*³fumarate

TABLE 6

Structure: Z-substituted benzothiazine with R³ on N, (CH₂)ₚ-R⁴ group, carbonyl, (4-methoxyphenyl)-O-(CH₂)ₘ-N(R⁵)(R⁶)

| compound No. | R³ | R⁴ | R⁵ | R⁶ | Z | m | p |
|---|---|---|---|---|---|---|---|
| 121*⁴ | —CH₃ | —H | —CH₃ | —CH₃ | —H | 3 | 1 |
| 122*⁴ | —CH₃ | —H | —CH₃ | —cyclohexyl (H) | —H | 5 | 1 |
| 123*⁴ | —CH₃ | —H | —CH₃ | —CH₃ | 7-CH₃ | 3 | 0 |

TABLE 6-continued

Structure: benzothiazine core with Z substituent, N-R3, C=O, (CH2)p-R4, and 2-position substituent being a phenyl with OCH3 and O-(CH2)m-N(R5)(R6)

| compound No. | R³ | R⁴ | R⁵ | R⁶ | Z | m | p |
|---|---|---|---|---|---|---|---|
| 124*³ | —CH₃ | —H | —CH₃ | cyclohexyl (H) | 7-CH₃ | 5 | 0 |
| 125*⁴ | —CH₃ | —H | —CH₃ | —CH₃ | 7-Cl | 3 | 0 |
| 126*⁴ | —CH₃ | —H | —CH₃ | cyclohexyl (H) | 7-Cl | 5 | 0 |
| 127*³ | —CH₃ | —H | —CH₃ | —(CH₂)₂—C₆H₃(OCH₃)₂ | —H | 4 | 1 |
| 128*¹ | —CH₃ | —CH(CH₃)₂ | —CH₃ | —(CH₂)₂—C₆H₃(OCH₃)₂ | —H | 4 | 0 |
| 129*¹ | —CH₃ | —OCH₃ | —CH₃ | —(CH₂)₂—C₆H₃(OCH₃)₂ | —H | 3 | 0 |
| 130*¹ | —CH₃ | —OCH₃ | —CH₃ | —(CH₂)₂—C₆H₃(OCH₃)₂ | —H | 4 | 0 |
| 131*¹ | —CH₃ | —SCH₃ | —CH₃ | —(CH₂)₂—C₆H₃(OCH₃)₂ | —H | 3 | 0 |
| 132*¹ | —CH₃ | —SCH₃ | —CH₃ | —(CH₂)₂—C₆H₃(OCH₃)₂ | —H | 4 | 0 |
| 133*¹ | —CH₃ | —SCH₃ | —CH₃ | —CH₂—CH(CH₃)—C₆H₃(OCH₃)₂ | —H | 3 | 0 |

TABLE 6-continued

[Structure: benzothiazine with Z substituent on benzene ring, S, N-R³, C=O, (CH₂)ₚ-R⁴, and central carbon bearing a 4-methoxyphenyl group with O-(CH₂)ₘ-N(R⁵)(R⁶) substituent]

| compound No. | R³ | R⁴ | R⁵ | R⁶ | Z | m | p |
|---|---|---|---|---|---|---|---|
| 134*[1] | —CH₃ | —SCH₃ | —CH₃ | —CH₂—CH(CH₃)—(3,4-dimethoxyphenyl) | —H | 4 | 0 |
| 135*[1] | —CH₃ | —SCH₃ | —CH₃ | —(CH₂)₂—(2,3-dimethoxyphenyl) | —H | 3 | 4 |
| 136*[1] | —CH₃ | —N(CH₃)COCH₃ | —CH₃ | —(CH₂)₂—(2,3-dimethoxyphenyl) | —H | 3 | 0 |
| 137*[1] | —CH₃ | —N(CH₃)COCH₃ | —CH₃ | —(CH₂)₂—(2,3-dimethoxyphenyl) | —H | 4 | 0 |
| 138*[3] | —CH₃ | —H | —CH₃ | —(CH₂)₂—(2,3-dimethoxyphenyl) | 7-CH₃ | 4 | 0 |
| 139*[4] | —CH₃ | —H | —CH₃ | —(CH₂)₂—(2,3-dimethoxyphenyl) | 7-Cl | 4 | 0 |
| 140*[1] | —CH₃ | —OCH₃ | —CH₃ | —(CH₂)₃—(2,3,4-trimethoxyphenyl) | —H | 3 | 0 |
| 141*[1] | —CH₃ | —SCH₃ | —CH₃ | —(CH₂)₃—(2,3,4-trimethoxyphenyl) | —H | 3 | 0 |
| 142*[1] | —CH₃ | —SCH₃ | —CH₃ | —(CH₂)₂—(2,3,5-trimethoxyphenyl) | —H | 4 | 0 |

TABLE 6-continued

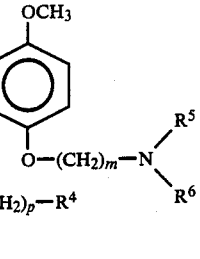

| compound No. | R³ | R⁴ | R⁵ | R⁶ | Z | m | p |
|---|---|---|---|---|---|---|---|
| 143*⁴ | —CH₃ | —H | —CH₃ | —(CH₂)₂O-(3,4-methylenedioxyphenyl) | —H | 3 | 1 |
| 144*⁴ | —CH₃ | —H | —CH₃ | —(CH₂)₂O-(3,4-methylenedioxyphenyl) | —H | 4 | 1 |
| 145*³ | —CH₃ | —CH(CH₃)₂ | —CH₃ | —(CH₂)₂O-(3,4-methylenedioxyphenyl) | —H | 3 | 0 |
| 146*³ | —CH₃ | —CH(CH₃)₂ | —CH₃ | —(CH₂)₂O-(3,4-methylenedioxyphenyl) | —H | 4 | 0 |
| 147*¹ | —CH₃ | —OCH₃ | —CH₃ | —(CH₂)₂O-(3,4-methylenedioxyphenyl) | —H | 3 | 0 |
| 148*¹ | —CH₃ | —OCH₃ | —CH₃ | —(CH₂)₂O-(3,4-methylenedioxyphenyl) | —H | 4 | 0 |
| 149*¹ | —CH₃ | —SCH₃ | —CH₃ | —(CH₂)₂O-(3,4-methylenedioxyphenyl) | —H | 3 | 0 |
| 150*⁵ | —CH₃ | —SCH₃ | —CH₃ | —(CH₂)₂O-(3,4-methylenedioxyphenyl) | —H | 4 | 0 |
| 151*¹ | —CH₃ | —N(CH₃)COCH₃ | —CH₃ | —(CH₂)₂O-(3,4-methylenedioxyphenyl) | —H | 3 | 0 |

TABLE 6-continued

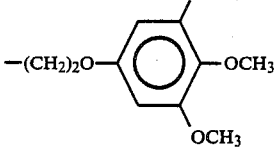

| compound No. | R³ | R⁴ | R⁵ | R⁶ | Z | m | p |
|---|---|---|---|---|---|---|---|
| 152*1 | —CH₃ | —N(CH₃)COCH₃ | —CH₃ | —(CH₂)₂O—[3,4-methylenedioxyphenyl] | —H | 4 | 0 |
| 153*4 | —CH₃ | —H | —CH₃ | —(CH₂)₂O—[3,4,5-trimethoxyphenyl] | —H | 3 | 1 |
| 154*4 | —CH₃ | —H | —CH₃ | —(CH₂)₂O—[3,4,5-trimethoxyphenyl] | —H | 4 | 1 |
| 155*1 | —CH₃ | —OCH₃ | | [cyclohexyl-CO-(4-methoxyphenyl)] | —H | 4 | 0 |
| 156*2 | —CH₃ | —N(CH₃)COCH₃ | | [piperazinyl]—N—CH₂—CH₂—OH | —H | 3 | 0 |

*¹hydrochloride
*²dihydrochloride
*³oxalate
*⁴fumarate
*⁵hydrochloride hemihydrate

TABLE 7

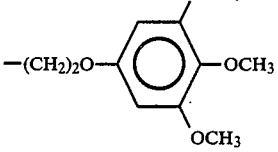

| compound No. | R³ | R⁵ | R⁶ | R⁷ | R⁸ | Z | m | p |
|---|---|---|---|---|---|---|---|---|
| 157*1 | —CH₃ | —CH₃ | —CH₃ | —CH₃ | —CH₃ | —H | 3 | 3 |
| 158*2 | —CH₃ | —CH₃ | —CH₃ | —CH₃ | —CH₃ | —H | 4 | 3 |

TABLE 7-continued

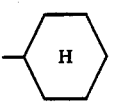

| compound No. | R³ | R⁵ | R⁶ | R⁷ | R⁸ | Z | m | p |
|---|---|---|---|---|---|---|---|---|
| 159*³ | —CH₃ | —CH₃ | 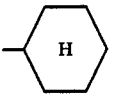 | —CH₃ | —CH₃ | —H | 3 | 3 |
| 160*⁴ | —CH₃ | —CH₃ | 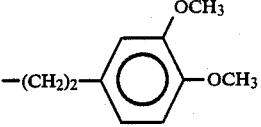 | —CH₃ | —CH₃ | —H | 4 | 3 |
| 161*² | —CH₃ | —CH₃ | 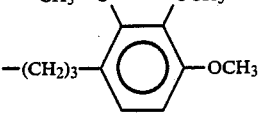 | —CH₃ | —CH₃ | —H | 4 | 3 |
| 162*⁴ | —CH₃ | —CH₃ | 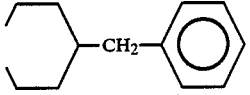 | —CH₃ | —CH₃ | —H | 4 | 3 |
| 163*² | —CH₃ | | 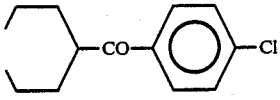 | —CH₃ | —CH₃ | —H | 3 | 3 |
| 164*² | —CH₃ | |  | —CH₃ | —CH₃ | —H | 3 | 3 |
| 165*² | —CH₃ | —CH₃ | —CH₃ | —CH₃ | —CH₃ | 7-Cl | 4 | 3 |
| 166*² | —CH₃ | —CH₃ | —CH₃ | | —CH₃ | 7-CH₃ | 3 | 3 |

*¹dioxalate ½ ethanol
*²dioxalate
*³dioxalate hemihydrate
*⁴dihydrochloride

PHARMACOLOGICAL ACTIVITIES

Calcium antagonists have not only potentially beneficial effects in the treatment of many diseases but also serve as valuable research tools to elucidate excitation-contraction coupling in various muscles types (A. Fleckenstein, Ann. Rev. Pharmacol., 17, 149–166, 1977). Therefore, we examined the calcium-antagonistic activity of the compounds of this invention.

Pharmacological test I

The action potentials on the smooth muscles of uterus, teania coli and portal vein are dependent on calcium ion, and therefore these smooth muscle preparations are useful for screening of calcium antagonists. We measured the calcium-antagonistic activity of the compounds by the method using guinea-pig teania coli preparation.

Isolated guinea-pig teania coli was suspended in a organ bath filled with Krebs solution at 32° C. and bubbled with 5% carbon dioxide in oxygen. After equilibration, the muscle was washed with $Ca^{++}$-free Krebs solution, and when the muscle had relaxed to the basal level, it was suspended in $Ca^{++}$-free-high-K Krebs solution.

The muscle was exposed to test compounds for 5 minutes before addition of CaCl$_2$, and the contraction induced by CaCl$_2$(3×10$^{-4}$M) was recorded isotonically. The calcium-antagonistic activity was represented by the concentration of test compound which elicited 50% inhibition of Ca$^{++}$-induced contraction (IC$_{50}$).

The compounds of this invention show superior calcium-antagonistic activities and the IC$_{50}$ values of numerous compounds are lower than 1×10$^{-5}$(M).

TABLE 8

| Calcium-antagonistic activity | |
|---|---|
| Compound No. | IC$_{50}$ (M) |
| 80 | 7.1 × 10$^{-7}$ |
| 83 | 8.6 × 10$^{-7}$ |
| 103 | 5.3 × 10$^{-7}$ |
| 131 | 6.3 × 10$^{-7}$ |
| 142 | 6.3 × 10$^{-7}$ |
| 147 | 4.2 × 10$^{-7}$ |
| 148 | 3.8 × 10$^{-7}$ |
| 150 | 8.9 × 10$^{-7}$ |

Blood platelet plays an important role not only in hemostasis but also in thrombosis. Platelet hyperaggregability leads to an increase in the number of circulating platelet aggregates, which may contribute toward the development of cardiac arrythmias, cardiac arrest or myocardial infarction. These cardiovascular diseases can be prevented by inhibition of platelet aggregation. Therefore, we screened the influence of test compounds on platelet aggregation in vitro, and found that they have an anti-aggregation activity.

Pharmacological test II

Blood was obtained from an anesthetized rabbit using 0.1 volumes of 3.8% sodium citrate as an anticoagulant. Platelet rich plasma(PRP) was isolated by centrifuge at 650 rpm for 10 minutes at room temperature. After preincubation of PRP (0.25 ml) with various concentrations of test compounds (14 μl) for 1 minute at 37° C., collagen (3 μg/ml: final concentration) or ADP (3 μM: final concentration) was added to induce aggregation and the aggregation profiles were monitored with a six-channel aggregometer(RIKADENKI). The control experiment contained saline instead of test compounds.

The anti-aggregation activity was represented by the concentration of test compounds which elicited 50% inhibition of control response.

The compounds of this invention show superior antiaggregatory activities and the IC$_{50}$ values of numerous compounds are lower than 1×10$^{-5}$(M).

The compounds of this invention can be administered either orally or parenterally. The dosage forms are tablet, capsule, granule, powder, suppository, injection, transdermal formulation, eye drops, etc. The dose is adjusted depending on sympton, dosage form, etc., but usual daily dosage is 1 to 5,000 mg, preferably 10 to 1,000 mg, in one or a few divided doses.

Examples of formulation are shown below.

(A) tablet

Following tablets were prepared by a direct compression of a mixture of the compound of this invention and excipient(s).

| | |
|---|---|
| compound No. 80 | 30 mg |
| lactose | 150 mg |
| crystalline cellulose | 50 mg |
| calcium carboxymethylcellulose | 7 mg |
| magnesium stearate | 3 mg |
| total | 240 mg |
| compound No. 83 | 50 mg |
| lactose | 120 mg |
| crystalline cellulose | 60 mg |
| low substituted hydroxypropylcellulose | 7 mg |
| magnesium stearate | 3 mg |
| total | 240 mg |
| compound No. 103 | 60 mg |
| lactose | 120 mg |
| crystalline cellulose | 60 mg |
| calcium carboxymethylcellulose | 7 mg |
| magnesium stearate | 3 mg |
| total | 250 mg |
| compound No. 131 | 40 mg |
| lactose | 150 mg |
| crystalline cellulose | 50 mg |
| calcium carboxymethylcellulose | 7 mg |
| magnesium stearate | 3 mg |
| total | 250 mg |
| compound No. 142 | 70 mg |
| lactose | 110 mg |
| crystalline cellulose | 60 mg |
| hydroxypropylcellulose | 7 mg |
| magnesium stearate | 3 mg |
| total | 250 mg |

The tablets may be treated with the common film-coating and furthur with sugar-coating.

(B) granule

| | |
|---|---|
| compound No. 147 | 30 mg |
| lactose | 385 mg |
| polyvinylpyrrolidone | 25 mg |
| hydroxypropylcellulose | 50 mg |
| magnesium stearate | 10 mg |
| total | 500 mg |
| compound No. 148 | 50 mg |
| lactose | 365 mg |
| polyvinylpyrrolidone | 25 mg |
| hydroxypropylcellulose | 50 mg |
| talc | 10 mg |
| total | 500 mg |

(C) powder

| | |
|---|---|
| compound No. 148 | 30 mg |
| lactose | 500 mg |
| starch | 440 mg |
| colloidal silica | 30 mg |
| total | 1000 mg |
| compound No. 150 | 50 mg |
| lactose | 250 mg |
| crystalline cellulose | 140 mg |
| magnesium stearate | 10 mg |
| total | 450 mg |

(D) capsule

| | |
|---|---|
| compound No. 80 | 30 mg |
| lactose | 100 mg |
| crystalline cellulose | 40 mg |
| hydroxypropylcellulose | 5 mg |
| magnesium stearate | 5 mg |
| total | 180 mg |
| compound No. 83 | 50 mg |
| glycerol | 329.8 mg |
| butyl benzoate | 0.2 mg |
| total | 380 mg |
| compound No. 103 | 20 mg |
| glycerol | 229.8 mg |
| butyl benzoate | 0.2 mg |
| total | 250 mg |

UTILITY IN AN INDUSTRY

The present invention offers novel compounds which posses antihypertensive effect, anti-platelet aggregation effect and calcium antagonism and are useful for treatment of circulartory diseases.

What we claim is:

1. A compound of the formula (I) and salts thereof,

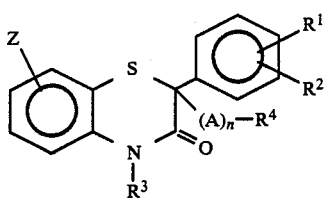 [I]

wherein

R¹ and R² are the same or different and are hydrogen, lower alkyl, hydroxy, lower alkoxy, lower alkanoyloxy, benzoyloxy tetrahydropyranyloxy, halogen, nitro, or

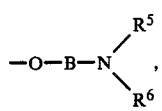

and the lower alkoxy group can be substituted by halogen, formyl, lower alkoxy or epoxy;

R³ is hydrogen or lower alkyl;

R⁴ is hydrogen, lower alkyl, hydroxy, lower alkoxy, mercapto, lower alkylthio, phenylthio, tolylthio, halogen, cyano, formyl-lower alkyl, lower alkoxy-lower alkyl or

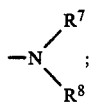

R⁵, R⁶, R⁷ and R⁸ are the same or different and are hydrogen, lower alkyl, cycloalkyl, lower alkanyol, benzoyl, or substituted lower alkyl, and the substituent(s) of the substituted lower alkyl is(are) hydroxy, phenyl, phenyloxy or phenylcarbonyl and such phenyl ring of the phenyl, phenyloxy or phenylcarbonyl group may further be resubstituted by lower alkyl, hydroxy, lower alkoxy, lower alkylenedioxy, halogen;

R⁵ and R⁶, and R⁷ and R⁸ may join to form piperidine or piperazine ring, and the piperidine or piperazine ring may be substituted by lower alkyl, phenyl, hydroxy-lower alkyl, phenyl-lower alkyl, phenyl bonyl, phenyl-(hydroxy)lower alkyl, phenyl-lower alkenylcarbonyl or naphthoxy-(hydroxy lower alkyl, and such phenyl ring of the phenyl, phenyl-lower alkyl, phenylcarbonyl, phenyl-(hydroxy)-lower alkyl or phenyl-lower alkenylcarbonyl group may further be resubstituted by lower alkyl, lower alkoxy, alkylenedioxy or halogen;

Z is hydrogen, lower alkyl, lower alkoxy, hydroxy, halogen;

A is straight or branched lower alkylene;

B is straight or branched lower alkylene which may be substituted by hydroxy; and n is 0 or 1, and when n is 0, both R⁴ and Z are not hydrogen atom at the same time, and when R⁴ is hydrogen or lower alkyl and R¹ or R² is

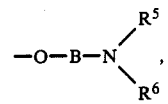

R⁵ or R⁶ is phenoxy-lower alkyl wherein the phenyl ring of said phenoxy-lower-alkyl group may be substituted with lower alkyl, hydroxy, lower alkoxy or lower alkylenedioxy.

2. The compound as in claim 1, wherein R¹ is hydroxy, lower alkoxy, lower alkanoyloxy, benzoyloxy, tetrahydropyranyloxy, lower alkoxy substituted by lower alkoxy, halogeno-lower alkoxy, formyl-lower alkoxy or epoxy-lower alkoxy.

3. The compound as in claim 1, wherein R² is hydrogen or lower alkoxy.

4. The compound as in claim 1, wherein R¹ is

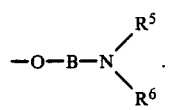

5. The compound as in claim 4, wherein B is lower alkylene.

6. The compound as in claim 4, wherein B is hydroxy-lower alkylene.

7. The compound as in claim 4, wherein R⁵ is lower alkyl.

8. The compound as in claim 4, wherein R⁶ is lower alkyl, cycloalkyl, lower alkyl substituted by lower alkoxy-phenyl or lower alkyl substituted by lower alkylenedioxy-phenyloxy.

9. The compound as in claim 4, wherein R⁵ and R⁶ join to form piperidine or piperazine ring.

10. The compound as in claim 9, wherein the substituent of piperidine ring is phenylcarbonyl, phenyl-lower alkyl, lower alkyl-phenylcarbonyl, lower alkoxy-phenylcarbonyl or halogenophenylcarbonyl.

11. The compund as in claim 9, wherein the substituent of piperazine ring is hydroxy-lower alkyl.

12. The compound as in claim 1, wherein R³ is hydrogen or lower alkyl.

13. The compound as in claim 1, wherein R⁴ is hydrogen, lower alkyl, lower alkoxy, hydroxy, halogen, cyano, formyl, lower alkylthio, phenylthio, tolylthio or lower alkoxy-lower alkyl.

14. The compound as in claim 1, wherein R⁴ is

15. The compound as in claim 14, wherein R⁷ is hydrogen or lower alkyl.

16. The compound as in claim 14, wherein R⁸ is lower alkyl, cycloalkyl, lower alkanoyl, benzoyl, lower alkyl substituted by lower alkylenephenyloxy or lower alkyl substituted by lower alkoxy-phenyl.

17. The compound as in claim 14, wherein R⁷ and R⁸ join to form piperidine or piperazine ring.

18. The compound as in claim 17, wherein the substituent of piperidine ring is phenylcarbonyl, lower alkyl-phenylcarbonyl, halogeno-phenylcarbonyl or phenyl-lower alkyl substituted by hydroxy.

19. The compound as in claim 17, wherein the substituent of piperazine ring is lower alkyl, lower alkyl substituted by lower alkoxy-phenyl, lower alkenoyl substituted by lower alkoxy-phenyl or naphthoxy-lower alkyl substituted by hydroxy.

20. The compound as in claim 1, wherein Z is hydrogen, lower alkyl or halogen.

21. 3,4-Dihydro-2-(2,5-dimethoxyphenyl)-4-methyl-2-[3-(N-methylcyclohexylamino)propyl]-3-oxo-2H-1,4-benzothiazine as in claim 1.

22. 3,4-Dihydro-2-(2,5-dimethoxyphenyl)-4-methyl-2-[3-(N-methyl-3,4,5-trimethoxyphenethylamino)-propyl]-3-oxo-2H-1,4-benzothiazine as in claim 1.

23. 3,4-Dihydro-4-methyl-2-[4-[4-(N-methyl-3,4-dimethoxyphenethylamino)butoxy]phenyl]-2-methylthio-3-oxo-2H-1,4-benzothiazine as in claim 1.

24. 3,4-Dihydro-2-[5-methoxy-2-[3-(N-methyl-3,4-dimethoxyphenethylamino)propoxy]phenyl]-4-methyl-2-methylthio-3-oxo-2H-1,4-benzothiazine as in claim 1.

25. 3,4-Dihydro-2-[5-methoxy-2-[4-(N-methyl-3,4,5-trimethoxyphenethylamino)butoxy]phenyl]-4-methyl-2-methylthio-3-oxo-2H-1,4-benzothiazine as in claim 1.

26. 3,4-Dihydro-2-methoxy-2-[5-methoxy-2-[3-(N-methyl-2-(3,4-methylenedioxyphenoxy)ethylamino]-propoxy]phenyl]-4-methyl-3-oxo-2H-1,4-benzothiazine as in claim 1.

27. 3,4-Dihydro-2-methoxy-2-[5-methoxy-2-[4-(N-methyl-2-(3,4-methylenedioxyphenoxy)ethylamino]-butoxy]phenyl]-4-methyl-3-oxo-2H-1,4-benzothiazine as in claim 1.

28. 3,4-Dihydro-2-[5-methoxy-2-[4-[N-methyl-2-(3,4-methylenedioxyphenoxy)ethylamino]butoxy]phenyl]-4-methyl-2-methylthio-3-oxo-2H-1,4-benzothiazine as in claim 1.

* * * * *

UNITED STATES PATENT AND TRADEMARK OFFICE
CERTIFICATE OF CORRECTION

PATENT NO. : 4,739,050

DATED : April 19, 1988

INVENTOR(S) : Jun-ichi Iwao et al.

It is certified that error appears in the above-identified patent and that said Letters Patent is hereby corrected as shown below:

On the title page, Item [19], "Jun-ichi et al." should read
-- Iwao et al. --. Item [75], should read:

-- [75] Iventors: Jun-ichi Iwao, Takarazuka; Tadashi Iso, Sakai; Masayuki Oya, Ibaraki, all of Japan --.

Signed and Sealed this

Thirtieth Day of August, 1988

Attest:

DONALD J. QUIGG

*Attesting Officer*     *Commissioner of Patents and Trademarks*